US007048908B2

(12) United States Patent
Basu et al.

(10) Patent No.: US 7,048,908 B2
(45) Date of Patent: May 23, 2006

(54) PARTICLES FOR INHALATION HAVING SUSTAINED RELEASE PROPERTIES

(75) Inventors: Sujit K. Basu, Cambridge, MA (US); Jeffrey Hrkach, Cambridge, MA (US); Michael Lipp, Framingham, MA (US); Katharina Elbert, Cambridge, MA (US); David A. Edwards, Cambridge, MA (US)

(73) Assignee: Advanced Inhalation Research, Inc., Cambridge, MA (US)

( * ) Notice: Subject to any disclaimer, the term of this patent is extended or adjusted under 35 U.S.C. 154(b) by 490 days.

(21) Appl. No.: 10/202,616

(22) Filed: Jul. 23, 2002

(65) Prior Publication Data

US 2003/0118513 A1 Jun. 26, 2003

Related U.S. Application Data

(63) Continuation of application No. 09/752,106, filed on Dec. 29, 2000, now abandoned.

(51) Int. Cl.
*A61K 9/12* (2006.01)
*A61K 9/127* (2006.01)

(52) U.S. Cl. .......................... 424/45; 424/46; 424/489; 424/499; 514/958

(58) Field of Classification Search .................. 424/45, 424/46, 489, 486, 499, 450; 514/958
See application file for complete search history.

(56) References Cited

U.S. PATENT DOCUMENTS

| | | | | |
|---|---|---|---|---|
| 2,470,296 | A | 5/1949 | Fields | 128/266 |
| 2,533,065 | A | 12/1950 | Taplin et al. | 167/65 |
| 2,992,645 | A | 7/1961 | Fowler | 128/208 |
| 3,781,230 | A | 12/1973 | Vassiliades et al. | 260/2.5 |
| 3,957,965 | A | 5/1976 | Hartley et al. | 424/14 |
| 4,009,280 | A | 2/1977 | Macarthur et al. | 424/283 |
| 4,089,800 | A | 5/1978 | Temple | 252/316 |
| 4,161,516 | A | 7/1979 | Bell | 424/14 |
| 4,173,488 | A | 11/1979 | Vassiliades et al. | 106/213 |
| 4,272,398 | A | 6/1981 | Jaffe | 252/316 |
| 4,352,883 | A | 10/1982 | Lim | 435/178 |
| 4,391,909 | A | 7/1983 | Lim | 435/178 |
| 4,466,442 | A | 8/1984 | Hilmann et al. | 128/653 |
| 4,480,041 | A | 10/1984 | Myles et al. | 436/508 |
| 4,524,769 | A | 6/1985 | Wetterlin | 128/203.15 |
| 4,572,203 | A | 2/1986 | Feinstein | 128/661 |
| 4,590,206 | A | 5/1986 | Forrester et al. | 514/456 |
| 4,615,697 | A | 10/1986 | Robinson | 604/890 |
| 4,679,555 | A | 7/1987 | Sackner | 128/203.15 |
| 4,741,872 | A | 5/1988 | De Luca et al. | 264/4.7 |
| 4,743,545 | A | 5/1988 | Torobin | 435/41 |
| 4,774,958 | A | 10/1988 | Feinstein | 128/660.01 |
| 4,789,550 | A | 12/1988 | Hommel et al. | 424/493 |
| 4,818,542 | A | 4/1989 | De Luca et al. | 424/491 |
| 4,847,091 | A | 7/1989 | Illum | 424/455 |
| 4,855,144 | A | 8/1989 | Leong et al. | 424/487 |
| 4,857,311 | A | 8/1989 | Domb et al. | 424/78 |
| 4,861,627 | A | 8/1989 | Mathiowitz et al. | 427/213.31 |
| 4,865,789 | A | 9/1989 | Castro et al. | 264/122 |
| 4,904,479 | A | 2/1990 | Illum | 424/490 |
| 4,917,119 | A | 4/1990 | Potter et al. | 131/273 |
| 4,976,968 | A | 12/1990 | Steiner | 424/491 |
| 4,994,281 | A | 2/1991 | Muranishi et al. | 424/497 |
| 5,033,463 | A | 7/1991 | Cocozza | 128/203.21 |
| 5,064,650 | A | 11/1991 | Lew | 424/435 |
| 5,069,936 | A | 12/1991 | Yen | 427/213.33 |
| 5,075,109 | A | 12/1991 | Tice et al. | 424/88 |
| 5,100,669 | A | 3/1992 | Hyon et al. | 424/426 |
| 5,123,414 | A | 6/1992 | Unger | 128/654 |
| 5,145,684 | A | 9/1992 | Liversidge et al. | 424/489 |
| 5,160,745 | A | 11/1992 | De Luca et al. | 424/487 |
| 5,169,871 | A | 12/1992 | Hughes et al. | 521/64 |
| 5,195,520 | A | 3/1993 | Schlief et al. | 128/660.02 |
| 5,204,108 | A | 4/1993 | Illum | 424/434 |
| 5,204,113 | A | 4/1993 | Hartley et al. | 424/45 |
| 5,260,306 | A | 11/1993 | Boardman et al. | 514/291 |
| 5,271,961 | A | 12/1993 | Mathiowitz et al. | 427/213.31 |
| 5,306,483 | A | 4/1994 | Mautone | 424/45 |

(Continued)

FOREIGN PATENT DOCUMENTS

CA 2085884 12/1991

(Continued)

OTHER PUBLICATIONS

Clay, M.M., et al. "Effect of Aerosol Particle Size on Bronchodilatation with Nebulised Terbutaline in Asthmatic Subjects," *Thorax* 41:364-368 (1986).

(Continued)

*Primary Examiner*—Sreeni Padmanabhan
*Assistant Examiner*—Mina Haghighatian
(74) *Attorney, Agent, or Firm*—Elmore Patent Law Group, PC; Carolyn S. Elmore

(57) ABSTRACT

The invention generally relates to a method for pulmonary delivery of therapeutic, prophylactic and diagnostic agents to a patient wherein the agent is released in a sustained fashion, and to particles suitable for use in the method. In particular, the invention relates to a method for the pulmonary delivery of a therapeutic, prophylactic or diagnostic agent comprising administering to the respiratory tract of a patient in need of treatment, prophylaxis or diagnosis an effective amount of particles comprising a therapeutic, prophylactic or diagnostic agent or any combination thereof in association with a charged lipid, wherein the charged lipid has an overall net charge which is opposite to that of the agent upon association with the agent. Release of the agent from the administered particles occurs in a sustained fashion.

47 Claims, 3 Drawing Sheets

U.S. PATENT DOCUMENTS

| | | | | |
|---|---|---|---|---|
| 5,327,883 | A | 7/1994 | Williams et al. | 128/203.12 |
| 5,334,381 | A | 8/1994 | Unger | 424/9 |
| 5,352,435 | A | 10/1994 | Unger | 424/9 |
| 5,384,133 | A | 1/1995 | Boyes et al. | 424/501 |
| 5,393,524 | A | 2/1995 | Quay | 424/9 |
| 5,407,609 | A | 4/1995 | Tice et al. | 264/46 |
| 5,456,917 | A | 10/1995 | Wise et al. | 424/426 |
| 5,466,841 | A | 11/1995 | Horrobin et al. | 554/79 |
| 5,482,946 | A | 1/1996 | Clark et al. | 514/291 |
| 5,518,709 | A | 5/1996 | Sutton et al. | 424/9.52 |
| 5,518,998 | A | 5/1996 | Bäckström et al. | 514/3 |
| 5,551,489 | A | 9/1996 | Trofast et al. | 141/18 |
| 5,607,695 | A | 3/1997 | Ek et al. | 424/468 |
| 5,612,053 | A | 3/1997 | Baichwal et al. | 424/440 |
| 5,690,954 | A | 11/1997 | Illum | 424/434 |
| 5,698,721 | A | 12/1997 | Heath | 554/80 |
| 5,707,644 | A | 1/1998 | Illum | 424/434 |
| 5,795,594 | A | 8/1998 | York et al. | 424/489 |
| 5,804,212 | A | 9/1998 | Illum | 424/434 |
| 5,814,607 | A | 9/1998 | Patton | 514/12 |
| 5,830,430 | A * | 11/1998 | Unger et al. | 425/5 |
| 5,830,853 | A | 11/1998 | Bäckström et al. | 514/4 |
| 5,851,453 | A | 12/1998 | Hanna et al. | 264/5 |
| 5,855,913 | A | 1/1999 | Hanes et al. | 424/489 |
| 5,874,064 | A | 2/1999 | Edwards et al. | 424/46 |
| 5,902,802 | A | 5/1999 | Heath | 514/76 |
| 5,985,309 | A | 11/1999 | Edwards et al. | 424/426 |
| 5,994,314 | A | 11/1999 | Eljamal et al. | 514/44 |
| 5,997,848 | A | 12/1999 | Patton et al. | 424/46 |
| 6,063,138 | A | 5/2000 | Hanna et al. | 23/295 R |
| 6,077,543 | A | 6/2000 | Gordon et al. | 424/489 |
| 6,136,295 | A | 10/2000 | Edwards et al. | 424/45 |
| RE37,053 | E | 2/2001 | Hanes et al. | 424/489 |
| 6,251,433 | B1 * | 6/2001 | Zuckermann et al. | 424/486 |
| 2002/0052310 | A1 | 5/2002 | Edwards et al. | |

FOREIGN PATENT DOCUMENTS

| | | |
|---|---|---|
| CA | 1300009 | 5/1992 |
| CA | 1302258 | 6/1992 |
| CA | 2166108 | 1/1995 |
| CA | 2170394 | 3/1995 |
| CA | 2111002 | 8/2000 |
| CA | 2058428 | 9/2000 |
| CA | 2126244 | 9/2000 |
| EP | 0 072 046 | 2/1983 |
| EP | 0 257 915 | 3/1988 |
| EP | 0 324 938 | 7/1989 |
| EP | 0 335 133 | 10/1989 |
| EP | 0 458 745 | 5/1991 |
| EP | 0 213 303 | 9/1991 |
| EP | 0 257 956 B1 | 5/1992 |
| EP | 0 510 731 A1 | 10/1992 |
| EP | 0 634 166 A1 | 1/1995 |
| EP | 0 656 206 A1 | 6/1995 |
| GB | 1 288 583 | 11/1969 |
| WO | WO 80/02365 | 11/1980 |
| WO | WO 88/04556 | 6/1988 |
| WO | WO 88/09163 | 12/1988 |
| WO | WO 91/04732 | 4/1991 |
| WO | WO 91/06286 | 5/1991 |
| WO | WO 91/06287 | 5/1991 |
| WO | WO 91/12823 | 9/1991 |
| WO | WO 92/18164 | 10/1992 |
| WO | WO 92/21382 | 12/1992 |
| WO | WO 93/25221 | 12/1993 |
| WO | WO 94/04133 | 3/1994 |
| WO | WO 94/07514 | 4/1994 |
| WO | WO 94/08627 | 4/1994 |
| WO | WO 94/16739 | 8/1994 |
| WO | WO 95/00127 | 1/1995 |
| WO | WO 95/07072 | 3/1995 |
| WO | WO 95/24183 | 9/1995 |
| WO | WO 95/35097 | 12/1995 |
| WO | WO 96/09814 | 4/1996 |
| WO | WO 96/15814 | 5/1996 |
| WO | WO 96/23485 | 8/1996 |
| WO | WO 96/40963 | 12/1996 |
| WO | WO 96/41873 | 12/1996 |
| WO | WO 97/36574 | 10/1997 |
| WO | WO 98/31346 | 7/1998 |
| WO | WO 98/51278 | 11/1998 |
| WO | WO 99/16419 | 4/1999 |
| WO | WO 99/16420 | 4/1999 |
| WO | WO 99/16421 | 4/1999 |
| WO | WO 99/16422 | 4/1999 |

OTHER PUBLICATIONS

Cohen, S., et al., "Controlled Delivery Systems for Proteins Based on Poly (Lactic/Glycolic Acid) Microspheres," *Pharm. Res.* 8(6):713-720 (1991).

Daly, W.H., et al., "The Preparation of N-Carboxyanhydrides of α-Amino Acids Using Bis(Trichloromethyl) Carbonate," *Tetrahedron Lett.*, 29(46):5859-5862 (1988).

Damms, B. and W. Bains, "The Cost of Delivering Drugs without Needles," *J. Controlled Release*, 8-11 (1996).

Davies, C.N., et al., "Breathing of Half-micron Aerosols. I. Experimental.," *J. of Appl. Physiol.* 32(5):591-600 (1972).

Dorries, A.M., and Valberg P.A., "Heterogeneity of Phagocytosis for Inhaled Versus Instilled Material," *Am. Rev. Respir. Dis.*, 146:811-837 (1992).

Kricheldorf, H.R. "α-Aminoacid-N-Carboxy-Anhydrides and Related Heterocycles," Springer-Verlag, Berlin (1987).

Edwards, D.A., "The Macrotransport of Aerosol Particles in the Lung: Aerosol Deposition Phenomena," *J. Aerosol Sci.*, 26(2):293-317 (1995).

Eldridge, J. H., et al., "Biodegradable Microspheres as a Vaccine Delivery System," *Mol. Immunol.*, 28(3):287-294 (1991).

Findeisen, W. "Uber Das Absetzen Kleiner, in Der Luft Suspendierter Teilchen in Der Menshlichen Lunge Bei Der Atmung," *Pflugers Arch. D. Ges. Physiol.* 236:367-379 (1935).

French, D.L, et al., "The Influence of Formulation on Emission, Deaggregation and Deposition of Dry Powders for Inhalation," *J. Aerosol Sci.*, 27(5):769-783 (1996).

Ganderton, D., "The Generation of Respirable Clouds Form Coarse Powder Aggregates," *J. Biopharmaceutical Sciences*, 3(1/2):101-105 (1992).

Gehr, P. et al., "Surfactant and Inhaled Particles in the Conducting Airways: Structural, Stereological, and Biophysical Aspects," *Microscopy Res. And Tech.*, 26:423-436 (1993).

Gerrity, T.R., et al., "Calculated Deposition of Inhaled Particles in the the Airway Generations of Normal Subjects," *J. Appl. Phys.*, 47(4):867-873 (1979).

Morén, F., "Aerosol Dosage Forms and Formulations," in *Aerosols in Medicine Principles, Diagnosis and Therapy*, Morén, et al., Eds, Elsevier, Amsterdam, 1985.

Morimoto, Y., and Adachi, Y., "Pulmonary Uptake of Liposomal Phosphatidylcholine Upon Intratracheal Administration to Rats," *Chem. Pharm. Bull.* 30(6):2248-2251 (1982).

Mulligan, R.C., "The Basic Science of Gene Therapy", *Science*, 260:926-932 (1993).

Mumenthaler, M., et al., "Feasibility Study on Spray-Drying Protein Pharmaceuticals: Recombinant human Growth Hormone and Tissue-Type Plasminogen Activator," *Pharm. Res.*, 11(1):12-20 (1994).
Niven, R.W., et al., "The Pulmonary Absorption of Aerosolized and Intratracheally Instilled rhG-CSF and monoPEGylated rhG-CSF," *Pharm. Res.*, 12(9):1343-1349 (1995).
Okumura, K., et al., "Intratracheal Delivery of Insulin. Absorption from Solution and Aerosol by Rat Lung," *Int. J. Pharmaceutics*, 88:63-73 (1992).
Patton, J.S., and R.M. Platz, "(D) Routes of Delivery: Case Studies (2) Pulmonary Delivery of Peptides and Proteins for Systemic Action", *Adv. Drug Del. Rev.*, 8:179-196 (1992).
Patton, J.S., et al., "Bioavailability of pulmonary delivered peptides and proteins: α-interferon, calcitonins and parathyriod hormones," *J. Controlled Release*, 28:79-85 (1994).
Pavia, D., "Lung Mucociliary Clearance". In *Aerosols and the Lung: Clinical and Experimental Aspects*, Clarke, S.W. and Pavia, D., eds. (Butterworths, London) , pp. 127-155, (1984).
Landahl, "On The Removal of Air-borne Droplets by The Human Respiratory Tract: I. The Lung," *Bull. Math. Biophys.*, 12:43-56 (1950).
Timsina, M.P., et al., "Drug Delivery to the Respiratory Tract Using Dry Powder Inhalers," *Int. J. of Pharm.*, 101:1-13 (1994).
Adjei, A., and Garren, J., "Pulmonary Delivery of Peptide Drugs: Effect of Particle Size on Bioavailability of Leuprolide Acetate in Healthy Male Volunteers," *Pharm. Res.*, 7(6):565-569 (1990).
Altshuler, B., et al., "Aerosol Deposition in the Human Respiratory Tract," *Am. Med. Assoc. Arch. of Indust. Health* 15:293-303 (1957).
Anderson, P.J., et al., "Effect of Cystic Fibrosis on Inhaled Aerosol Boluses," *Am. Rev. Respir. Dis.*, 140:1317-1324 (1989).
Pinkerton, K.E., et al., "Aerosolized Fluorescent Microspheres Detected in the Lung Using Confocal Scanning Laser Microscopy", *Microscopy Res. and Tech.*, 26:437-443 (1993).
Colthorpe, P., et al., "The Pharmacokinetics of Pulmonary-Delivered Insulin: A Comparison of Intratracheal and Aerosol Administration to the Rabbit," *Pharm. Res.* 9(6):764-768 (1992).
Rudt, S., and R.H. Muller, "In Vitro Phagocytosis Assay of Nano- and Microparticles by Chemiluminescence. I. Effect of Analytical Parameters, Particle Size and Particle Concentration," *J. Contr. Rel.*, 22:263-271 (1992).
Rudt, S., et al., "In Vitro Phagocytosis Assay of Nano- and Microparticles by Chemiluminescence. IV. Effect of Surface Modification by Coating of Particles with Poloxamine and Antarox CO on the Phagocytic Uptake", *J. of Contr. Rel.* 25:123-132 (1993).
Ruffin, R.E., et al., "The Preferential Deposition of Inhaled Isoproterenol and Propranolol in Asthmatic Patients," *Chest* 80(6):904-907 (1981).
Sela, M., et al., "Multichain Polyamino Acids," *J. Am. Chem. Soc.*, 78:746-751 (1956).
Tabata, Y., et al., "Controlled Delivery Systems for Proteins Using Polyanhydride Microspheres," *Pharm. Res.* 10(4):487-496 (1993).
Swift, D., "The Oral Airway—A Conduit or Collector for Pharmaceutical Aerosols?" *Respiratory Drug Delivery IV*, 187-195 (1994).
Tabata, Y., and Y. Ikada, "Effect of Surface Wettability of Microspheres on Phagocytosis," *J. of Colloid and Interface Sci.*, 127(1):132-140 (1989).
Tabata, Y., and Y. Ikada, "Macrophage Phagocytosis of Biodegradable Microspheres Composed of L-lactic Acid/glycolic Acid Homo- and Copolymers," *J. of Biomed. Mater. Res.*, 22:837-858 (1988).
Tabata, Y., and Ikada, Y., "Effect of Size and Surface Charge of Polymer Microspheres on Their Phagocytosis by Macrophage," *J. Biomed. Mater. Res.*, 22:837-843 (1988).
Allen, T.M., et al., "Subcutaneous Administration of Liposomes: A Comparison with the Intravenous and Intraperitoneal Routes of Injection," *Biochem. et Biophys. Acta.* 1150:9-16 (1993).
Barrera, D.A., et al., "Synthesis and RGD Peptide Modification of a New Biodegradable Copolymer: Poly(lactic acid-co-lysine) ," *J. Am. Chem. Soc.*, 115:11010-11011 (1993).
Tansey, I.P., "The Challenges in the Development of Metered Dose Inhalation Aerosols Using Ozone-Friendly Propellants," *Spray Technol. & Market*, 4:26-29 (1994).
Turner, J.R., and S.V. Hering, "Greased and Oiled Substrates as Bounce-Free Impaction Surfaces," *J. Aerosol Sci.*, 18(2):215-224 (1987).
Lai, Y-L., et al., "Sustained Bronchodilation with Isoproterenol Poly(Glycolide-co-Lactide) Microspheres," *Pharm. Res.*, 10(1):119-125 (1993).
Visser, J., "An Invited Review: Van der Waals and Other Cohesive Forces Affecting Power Fluidization," Powder Technology, 58:1-10 (1989).
Wall, D.A., "Pulmonary Absorption of Peptides and Proteins," *Drug Delivery*, 2:1-20 (1995).
Warheit, D.B., and Hartsky, M.A., "Role of Alveolar Macrophage Chemotaxis and Phagocytosis in Pulmonary Clearance to Inhaled Particles: Comparisons Among Rodent Species," *Microscopy Res. and Tech.*, 26:412-422 (1993).
Langer, R., "New Methods of Drug Delivery", *Science*, 249:1527-1533 (1990).
Wong, M., and Suslick, K.S., "Sonochemically Produced Hemoglobin Microbubbles," *Mat. Res. Soc. Symp. Proc.*, 372:89-95 (1995).
Zanen, P., et al., "The Optimal Particle Size for β-adrenergic Aerosols in Mild Asthmatics", *Int. J. of Pharm.*, 107:211-217 (1994).
Zanen, P., et al., "The Optimal Particle Size for Parasympathicolytic Aerosols in Mild Asthmatics", *Int. J. of Pharm.*, 114:111-115 (1995).
Zeng, X.M., et al., "The Controlled Delivery of Drugs to the Lung," *Int. J. of Pharm.*, 124:149-164 (1995).
Kohler, D., "Aerosols for Systemic Treatment" *Lung*, Suppl: pp. 677-684 (1990).
Anderson, M., et al., "Human Deposition and Clearance of 6-μm Particles Inhaled with an Extremely Low Flow Rate," *Exp. Lung Res.*, 21:187-195 (1995).
Beck, L.R., et al., "A New Long-Acting Injectable Microcapsule System for the Administration of Progesterone," *Fertility and Sterility*, 31(5):545-551 (1979).
Brown, A.R., et al., "Propellant-Driven Aerosols of Functional Proteins as Potential Therapeutic Agents in the Respiratory Tract," *Immunopharmacology*, 28:241-257 (1994).
Carroll, B.A., et al., "Gelatin Encapsulated Nitrogen Microbubbles as Ultrasonic Contrast Agents," *Investigative Radiology*, 15:260-266 (1980).

Carroll, B.A., et al., "Ultrasonic Contrast Enhancement of Tissue by Encapsulated Microbubbles," *Radiology*, 143:747-750 (1982).
Ch'ng, H.S., et al., "Bioadhesive Polymers as Platforms for Oral Controlled Drug Delivery II: Synthesis and Evaluation of Some Swelling, Water-Insoluble Bioadhesive Polymers," *J. of Pharm Sci*., 74(4):399-405 (1985).
Clark, A., and P. Byron, "Dependence of Pulmonary Absorption Kinetics on Aerosol Particle Size," *Z. Erkrank. Atm. org*., 166:13-24 (1986).
Darquenne, C., and M. Paiva, "Two and Three-Dimensional Simulations of Aerosol Transport and Deposition in Alveolar Zone of Human Lung," *Journal of Applied Physiology*, 80(4):1401-1414 (1996).
Davis, S.S., and L. Illum, "Polymeric Microspheres as Drug Carriers," *Biomaterials*, 9:111-115 (1988).
Davis, S.S., et al., "Microspheres as Controlled-Release Systems for Parenteral and Nasal Administration," *Controlled Release Technology*, Chapter 15, pp. 201-213 (1987).
Edwards, D.A., et al., "Large Porous Particles for Pulmonary Drug Delivery," *Science* 276:1868-71 (1997).
Feinstein, S.B., et al., "Two-Dimensional Contrast Echocardiography I. In Vitro Development and Quantitative Analysis of Echo Contrast Agents," *JACC* 3(1):14-20 (1984).
Ferin, J., et al., "Pulmonary Retention of Ultrafine and Fine Particles in Rats," *Am. J. Respir. Cell Mol. Biol. 6*:535-542 (1992).
Gurny, R., et al., "Bioadhesive Intraoral Release Systems: Design, Testing and Analysis," *Biomaterials*, 5:336-340 (1984).
Illum, L., et al., "Bioadhesive Microspheres as a Potential Nasal Drug Delivery System," *Int. J. of Pharm*. 39:189-199 (1987).
Kao, Y.J., and R.L. Juliano, "Interactions of Liposomes with the Reticuloendothelial System, Effects of Reticuloendothelial Blockade on the Clearance of Large Unilamellar Vesicles," *Biochimica et Biophys. Acta*. 677:453-461 (1981).
Lai, W.C., et al., "Protection Against *Mycoplasma pulminosis* Infection by Genetic Vaccination," *DNA and Cell Biology*, 14(7):643-651 (1995).
Benita, S., et al., "Characterization of Drug-loaded Poly (d,1-lactide) Microspheres," *J. of Pharm. Sci* 73(12):1721-1724 (1984).
Taburet, A.M., and Schmit, B., "Pharmacokinetic Optimisation of Asthma Treatment," *Clin. Pharmacokinet*. 26(5):396-418 (1994).
Wheatley,M.A., et al., "Contrast Agents for Diagnostic Ultrasound: Development and Evaluation of Polymer-Coated Microbubbles," *Biomaterials* 11:713-717 (1990).
Wichert, B., and Rohdewald, P., "Low Molecular Weight PLA: A Suitable Polymer for Pulmonary Administered Microparticles?," *J. Microencapsulation*, 10(2):195-207 (1993).
Hanes, J., et al., "Porous Dry-powder PLGA Microspheres Coated with Lung Surfactant for Systemic Insulin Delivery Via the Lung," *Proc. Int. Symp. Control. Rel. Bioact. Mater*., 24:57-58 (1997).
Zeng, X.M., et al., "Tetrandrine Delivery to the Lung: The Optimisation of Albumin Microsphere Preparation by Central Composite Design," *Int. J. of Pharm*., 109:135-145 (1994).
Ménache, M.G., et al., "Particle Inhalability Curves for Humans and Small Laboratory Animals," *Annals of Occupational Hygiene*, 39(3):317-328 (1995).
Newman, S.P., "Therapeutic Inhalation Agents and Devices," *Inhalation Therapy*, 76(5):194-207 (1984).
Newman, S.P., "Aerosol Deposition Considerations in Inhalation Therapy," *Chest*, 88(2):152S-160S (1985).
New, R.R.C., "Characterization of Liposomes," in *Liposomes: A Practical Approach, R. New*, Editor, IRL Press, New York, 105-161 (1990).
Niven, R.W., et al., "Solute Absorption From the Airways of the Isolated Rat Lung. III. Absorption of Several Peptidase-Resistant, Synthetic Polypeptides: Poly-(2-Hydroxyethyl)-Aspartamides," *Pharm. Res*., 7(10):990-994 (1990).
Niwa, T., et al., "Aerosolization of Lactice/Glycolide Copolymer (PLGA) Nanospheres for Pulmonary Delivery of Peptide-Drugs," *Yakugaku Zasshi*, 115(9):732-741 (1995).
Ogiwara, M., "Clearance and Maximum Removal Rate of Liposomes in Normal and Impaired Liver of Rat," *Gastroenterologia Japonica*, 19(1):34-40 (1984).
Smith, A.L., and B. Ramsey, "Aerosol Administration of Antibiotics," *Respiration, 62* (*suppl l*):19-24 (1995).
Smith, P.L., "Peptide Delivery via the Pulmonary Route: A Valid Approach for Local and Systemic Delivery," *J. of Contr. Rel*., 46:99-106 (1997).
Strand, S.E., and L. Bergqvist, "Radiolabeled Colloids and Macromolecules in the Lymphatic System," *Critical Reviews in Therapeutic Drug Carrier Systems*, 6(3):211-238 (1989).
Blackett, P.M., and G. Buckton, "A Microcalorimetric Investigation of the Interaction of Surfactants with Crystalline and Partially Crystalline Salbutamol Sulphate in a Model Inhalation Aerosol System," *Pharmaceutical Research*, 12(11):1689-1693 (1995).
Brain, J.D., "Physiology and Pathophysiology of Pulmonary Macrophages". In *The Reticuloendothelial System*, Reichard and Filkins, eds. (Plenum Press, New York), pp. 315-327 (1985).
Byron, P.R., "Determinants of Drug and Polypeptide Bioavailability from Aerosols Delivered to the Lung," *Adv. Drug. Del. Rev*., 5:107-132 (1990).
Clark, A.R., and M. Egan, "Modeling the Deposition of Inhaled Powdered Drug Aerosols," *J. Aerosol Sci*., 25(1):175-186 (1994).
Le Corre, P., et al., "Preparation and Characterization of Bupivacaine-Loaded Polylactide and Polylactide-Co-Glycolide Microspheres," *Int. J. of Pharmaceutics*, 107:41-49 (1994).
Leone-Bay, A., et al., "Microsphere Formation in a Series of Derivatized α-Amino Acids: Properties, Molecular Modeling, and Oral Delivery of Salmon calcitonin," *J. of Med. Chem*., 38(21):4257-4262 (1995).
Liu, F., et al., "Pulmonary Delivery of Free and Liposomal Insulin," *Pharm. Res*. 10(2):228-232 (1993).
Liu, W.R., et al., "Moisture-Induced Aggregation of Lyophilized Proteins in the Solid State," *Biotechnol. and Bioeng*., 37:177-184 (1991).
Martonen, T.B., "Mathematical Model for the Selective Deposition of Inhaled Pharmaceuticals", *J. of Pharm. Sci*., 82(12):1191-1198 (1993).
Masinde, L.E., and Hickey, A.J., "Aerosolized Aqueous Suspensions of Poly (L-Lactic Acid) Microspheres," *Int. J. of Pharmaceutics*, 100:123-131 (1993).

Mathiowitz, E., et al., "Novel Microcapsules for Delivery Systems," *Reactive Polymers*, 6:275-283 (1987).
Mathiowitz, E., et al., "Polyanhydride Microspheres. IV. Morphology and Characterization of Systems Made by Spray Drying," *J. of Appl. Polymer Sci.* 45:125-134 (1992).
Mathiowitz, E., et al., "Morphology of Polyanhydride Microsphere Delivery Systems," *Scanning Microscopy*, 4(2):329-340 (1990).
Mathiowitz, E., and R. Langer, "Polyanhydride Microspheres as Drug Carriers I. Hot-Melt Microencapsulation," *J. of Controlled Release* 5:13-22 (1987).
Mathiowitz, E., et al., "Polyanhydride Microspheres as Drug Carriers. II. Microencapsulation by Solvent Removal," *J. of Appl. Polymer Sci.*, 35:755-774 (1988).
Davies, et al., "Breathing of half-micron aerosols. I. Experimental," *J. Appl. Physiol.* 32(5):591-600 (1972).
Kwok, K.K., et al., "Production of 5-15 μm Diameter Alginate Polylysine Microcapsules by an Air Atomization Technique," Pharm. Res., 8(3):341-344 (1991).
Gonda, I., "Aerosols for Delivery of Therapeutic and Diagnostic Agents to the Respiratory Tract," in *Critical Reviews in Therapeutic Drug Carrier Systems*, 6:273-313 (1990).
Gonda, I., "Preface. Major Issues and Future Prospects in the Delivery of Therapeutic and Diagnostic Agents to the Respiratory Tract," *Adv. Drug Del. Rev.* 5:1-9 (1990).
Gonda, I., "Physico-chemical Principles in Aerosol Delivery," in *Topics in Pharmaceutical Sciences* 1991, Crommelin, D.J. and K.K. Midha, Eds., Medpharm Scientific Publishers, Stuttgart, pp. 95-117 (1992).
Gonda, I., "Targeting by Deposition," in Pharmaceutical Inhalation Aersol Technology (ed. A.J. Hickey), Marcel Dekkar Inc., pp. 61-82, New York (1992).
Heyder, J., et al., "Deposition of Particles in the Human Respiratory Tract in the Size Range 0.005-15 μm," *J. Aerosol. Sci.*, 17(3):811-825 (1996).
Heyder, J., and G. Rudolf, "Mathematical models of particle deposition in the human respiratory tract," *J. Aerosol Sci.*, 15:697-707 (1984).
Heyder, J., et al., "Total Deposition of Aerosol Particles in the Human Respiratory Tract for Nose and Mouth Breathing," *J. Aerosol Sci.*, 6:311-328 (1975).
Hickey, A.J., et al., "Use of Particle Morphology to Influence the Delivery of Drugs from Dry Powder Aerosols," *J. Biopharmaceutical Sci.*, 3 (1 / 2):107-113 (1992).
Hirano, S., et al., "Pulmonary Clearance and Toxicity of Zinc Oxide Instilled into the Rat Lung," *Arch. of Toxicology*, 63:336-342 (1989).
Hrkach, et al., "Synthesis of Poly(L-lactic acid-co-L-lysine) Graft Copolymers:" *Macromolecules*, 28(13):4736-4739 (1995).
Hrkach, J.S., et al., "Poly(L-Lactic acid-co-amino acid) Graft Copolymers: A Class of Functional Biodegradable Biomaterials" in Hydrogels and Biodegradable Polymers for Bioapplications, ACS Symposium Series No. 627, Raphael M. Ottenbrite, et al., Eds., Americal Chemical Society, Chapter 8, pp. 93-101, 1996.
Illum, "Bioadhesive Microspheres as a Potential Controlled Release Nasal Drug Delivery System," *International J. of Pharm.*, 39:189-199 (1987).
Johnson, M.A., et al. "Delivery of Albuterol and Ipratrophiumbromide from Two Nebulizer Systems in Chronic Stable Asthma: Efficacy and Pulmonary Deposition," *Chest*, 96:6-10 (1989).
Kassem, N.M., and D. Ganderton, "The Influence of Carrier Surface on the Characteristics of Inspirable Powder Aerosols," *J. Pharm. Pharmacol.*, 42(Supp):11 (1990).
Kawaguchi, H. et al., "Phagocytosis of Latex Particles by Leukocytes. I. Dependence of Phagocytosis on the Size and Surface Potential of Particles," *Biomaterials* 7:61-66 (1986).
Kobayashi, S. et al., "Pulmonary Delivery of Salmon Calcitonin Dry Powders Containing Absorption Enhancers in Rats," *Pharm. Res.*, 13(1):80-83 (1996).
Komanda, F. et al., Intratracheal Delivery of Peptide and Protein Agents: Absorption from Solution and Dry Powder by Rat Lung, *J. Pharm. Sci.*, 83(6):863-867 (Jun., 1994).
Krenis, L.J. and B. Strauss, "Effect of Size and Concentration of Latex Particles on Respiration of Human Blood Leucocytes," *Proc. Soc. Exp. Med.*, 107:748-750 (1961).

* cited by examiner

PARTICLES FOR INHALATION HAVING SUSTAINED RELEASE PROPERTIES

RELATED APPLICATIONS

This application is a continuation of U.S. application Ser. No. 09/752,106, filed Dec. 29, 2000, now abandoned which relates to application Ser. No. 09/337,245, filed on Jun. 22, 1999, Ser. No. 09/383,054, filed on Aug. 25, 1999, Ser. No. 09/382,959, filed on Aug. 25, 1999, Ser. No. 09/644,320, filed on Aug. 23, 2000, Ser. No. 09/665,252 filed on Sep. 19, 2000, Ser. No. 09/644,105, filed on Aug. 23, 2000, Ser. No. 09/644,736 filed on Aug. 23, 2000 and Ser. No. 09/591,307 filed on Jun. 9, 2000.

This application also relates to application Ser. No. 09/394,233 filed on Sep. 13, 1999, which is a continuation of application Ser. No. 08/971,791 filed on Nov. 17, 1997, now U.S. Pat. No. 5,985,309.

The entire contents of the above-reference applications are hereby incorporated by reference.

BACKGROUND OF THE INVENTION

Pulmonary delivery of bioactive agents, for example, therapeutic, diagnostic and and prophylactic agents provides an attractive alternative to, for example, oral, transdermal and parenteral administration. That is, pulmonary administration can typically be completed without the need for medical intervention (self-administration), the pain often associated with injection therapy is avoided, and the amount of enzymatic and pH mediated degradation of the bioactive agent, frequently encountered with oral therapies, can be significantly reduced. In addition, the lungs provide a large mucosal surface for drug absorption and there is no first-pass liver effect of absorbed drugs. Further, it has been shown that high bioavailability of many molecules, for example, macromolecules, can be achieved via pulmonary delivery or inhalation. Typically, the deep lung, or alveoli, is the primary target of inhaled bioactive agents, particularly for agents requiring systemic delivery.

The release kinetics or release profile of a bioactive agent into the local and/or systemic circulation is a key consideration in most therapies, including those employing pulmonary delivery. That is, many illnesses or conditions require administration of a constant or sustained levels of a bioactive agent to provide an effective therapy. Typically, this can be accomplished through a multiple dosing regimen or by employing a system that releases the medicament in a sustained fashion.

However, delivery of bioactive agents to the pulmonary system typically results in rapid release of the agent following administration. For example, U.S. Pat. No. 5,997,848 to Patton et al. describes the rapid absorption of insulin following administration of a dry powder formulation via pulmonary delivery. The peak insulin level was reached in about 30 minutes for primates and in about 20 minutes for human subjects. Further, Heinemann, Traut and Heise teach in Diabetic Medicine 14:63–72 (1997) that the onset of action, assessed by glucose infusion rate, in healthy volunteers after inhalation was rapid with the half-maximal action reached in about 30 minutes.

As such, a need exists for formulations suitable for inhalation comprising bioactive agents and wherein the bioactive agent of the formulation is released in a sustained fashion into the systemic and/or local circulation.

SUMMARY OF THE INVENTION

This invention is based upon the unexpected discovery that combining a charged agent with a lipid carrying an opposite charge results in a sustained release profile of the agent.

The invention generally relates to a method for pulmonary delivery of therapeutic, prophylactic and diagnostic agents to a patient wherein the agent is released in a sustained fashion, and to particles suitable for use in the method. In particular, the invention relates to a method for the pulmonary delivery of a therapeutic, prophylactic or diagnostic agent comprising administering to the respiratory tract of a patient in need of treatment, prophylaxis or diagnosis an effective amount of particles comprising a therapeutic, prophylactic or diagnostic agent or any combination thereof in association with a charged lipid, wherein the charged lipid has an overall net charge which is opposite to that of the agent upon association with the agent. Release of the agent from the administered particles occurs in a sustained fashion.

In one embodiment, the association of the therapeutic, prophylactic or diagnostic agent and the oppositely charged lipid can result from ionic complexation. In another embodiment, association of the therapeutic, prophylactic or diagnostic agent and the oppositely charged lipid can result from hydrogen bonding.

In yet a further embodiment, the association of the therapeutic, prophylactic or diagnostic agent and the oppositely charged lipid can result from a combination of ionic complexation and hydrogen bonding.

The particles suitable for use in the method can comprise a therapeutic, prophylactic or diagnostic agent in association with a charged lipid having a charge opposite to that of the agent. The charges are opposite upon association, prior to administration. In a preferred embodiment, the charges of the agent and lipid upon association, prior to administration, are those which the agent and lipid possess at pulmonary pH.

For example, the particles suitable for pulmonary delivery can comprise a therapeutic, prophylactic or diagnostic agent which possesses an overall net negative charge, in association with a lipid which possesses an overall net positive charge. For example, the agent can be insulin which has an overall net charge which is negative and the lipid can be 1,2-dipalmitoyl-sn-glycero-3-ethylphosphatidylcholine (DPePC).

Alternatively, the particles suitable for pulmonary delivery can comprise a therapeutic, prophylactic or diagnostic agent which possesses an overall net positive charge in association with a lipid which possesses an overall net negative charge. For example, the agent can be albuterol which possesses an overall positive charge and the lipid can be 1,2-dipalmitoyl-sn-glycero-3-[phospho-rac-(1-glycerol)] (DPPG) which possesses an overall net negative charge.

Further, the particles suitable for pulmonary delivery can comprise a therapeutic, prophylactic or diagnostic agent which has an overall net charge which can be modified by adjusting the pH of a solution of the agent, prior to association with the lipid. For example, at a pH of about 7.4 insulin has an overall net charge which is negative. Therefore, insulin and a positively charged lipid can be associated at this pH prior to administration to prepare a particle having an agent in association with a charged lipid wherein the charged lipid has a charge opposite to that of the agent. However, the charges on insulin can also be modified, when in solution, to possess an overall net charge which is positive by modifying the pH of the solution to be less than the pIof insulin (pI=5.5). As such, when insulin is in solution at a pH of about 4, for example, it will possess an overall net charge which is positive. As this is the case, the positively charged insulin can be associated with a negatively charged lipid, for example, 1,2-distearoyl-sn-glycero-3-[phospho-rac-(1-glycerol)] (DSPG).

Modification of the charge of the therapeutic, prophylactic or diagnostic agent prior to association with the charged lipid, can be accomplished with many agents, particularly, proteins. For example, charges on proteins can be modulated by spray drying feed solutions below or above the isoelectric points (pI) of the protein. Charge modulation can also be accomplished for small molecules by spray drying feed solutions below or above the pKa of the molecule.

In a particular embodiment, the particles of the invention comprise more than one lipid, more than one bioactive agent or both. Also charged lipids can be combined with lipids without a net charge.

The particles, can further comprise a carboxylic acid which is distinct from the bioactive agent and lipid. In one embodiment, the carboxylic acid includes at least two carboxyl groups. Carboxylic acids, include the salts thereof as well as combinations of two or more carboxylic acids and/or salts thereof. In a preferred embodiment, the carboxylic acid is a hydrophilic carboxylic acid or salt thereof. Citric acid and citrates, such as, for example sodium citrate, are preferred. Combinations or mixtures of carboxylic acids and/or their salts also can be employed.

The particles suitable for use in the invention can further comprise a multivalent salt or its ionic components. In a preferred embodiment, the salt is a divalent salt. In another preferred embodiment, the salt is a salt of an alkaline-earth metal, such as, for example, calcium chloride. The particles of the invention can also include mixtures or combinations of salts and/or their ionic components.

The particles suitable for use in the invention can further comprise an amino acid. In a preferred embodiment the amino acid is hydrophobic.

The particles, also referred to herein as powder, can be in the form of a dry powder suitable for inhalation. The particles can have a tap density of less than about 0.4 g/cm$^3$, preferably less than about 0.1 g/cm$^3$. Further, the particles suitable for use in the invention can have a median geometric diameter of from about 5 micrometers to about 30 micrometers. In yet another embodiment, the particles suitable for use in the invention have an aerodynamic diameter of from about 1 to about 5 micrometers.

The invention has numerous advantages. For example, particles suitable for inhalation can be designed to possess a sustained release profile. This sustained released profile provides for prolonged residence of the administered bioactive agent in the lung and increases the amount of time in which therapeutic levels of the agent are present in the local environment or systemic circulation. The sustained release of agent provides a desirable alternative to injection therapy currently used for many therapeutic, diagnostic and prophylactic agent requiring sustained release of agent, such as insulin for the treatment of diabetes. In addition, the invention provides a method of delivery to the pulmonary system wherein the high initial release of agent typically seen in inhalation therapy is reduced. Consequently, patient compliance and comfort can be increased by not only reducing frequency of dosing, but by providing a therapy which is more amenable to patients.

Figure 1:
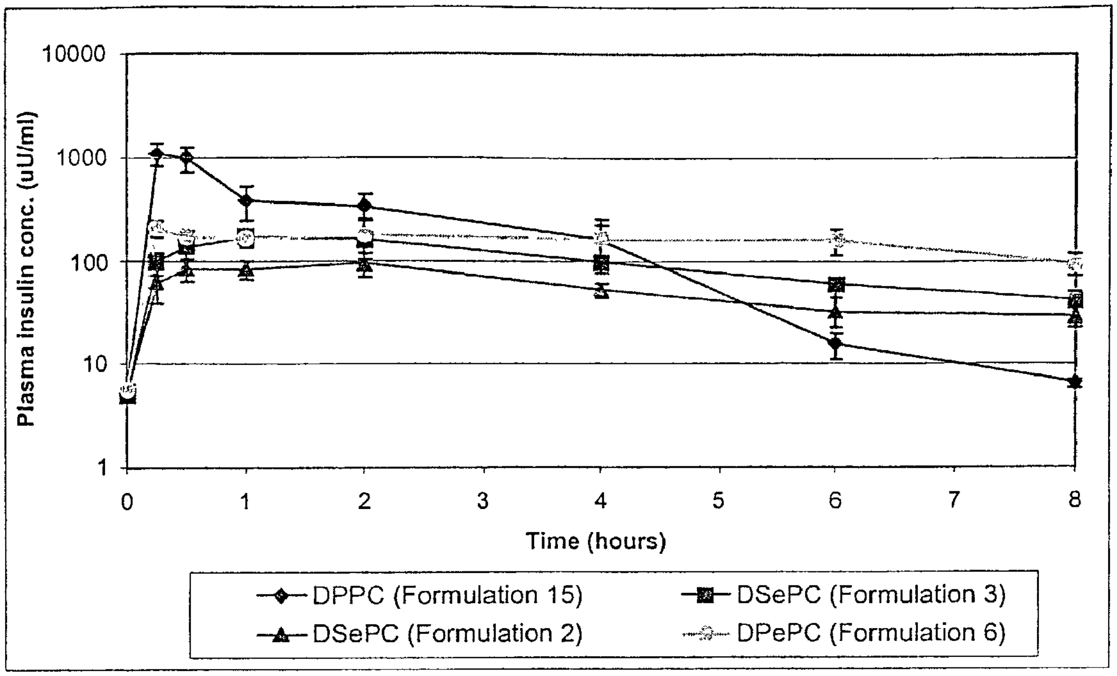
FIG. 1 is a graph showing the in vivo release profile of dry powder formulations comprising insulin and either a lipid (DPPC) with no overall net a charge or lipid having an overall net charge opposite to that of insulin (DSePC and DPePC).

The foregoing and other objects, features and advantages of the invention will be apparent from the following more particular description of preferred embodiments of the invention, as illustrated in the accompanying drawings. The drawings are not necessarily to scale, emphasis instead being placed upon illustrating the principles of the invention.

DETAILED DESCRIPTION OF THE INVENTION

A description of preferred embodiments of the invention follows.

Therapeutic, prophylactic or diagnostic agents, can also be referred to herein as "bioactive agents", "medicaments" or "drugs".

The invention relates to a method for the pulmonary delivery of therapeutic, prophylactic and diagnostic agents comprising administering to the respiratory tract of a patient in need of treatment, prophylaxis or diagnosis an effective amount of particles comprising a therapeutic, prophylactic or diagnostic agent or any combination thereof in association with a charged lipid, wherein the charged lipid has an overall net charge which is opposite to that of the agent. The agent is released from the administered particles in a sustained fashion.

The particles of the invention release bioactive agent in a sustained fashion. As such, the particles possess sustained release properties. "Sustained release", as that term is used herein, refers to a release of active agent in which the period of release of an effective level of agent is longer than that seen with the same bioactive agent which is not associated with an oppositely charged lipid, prior to administration. In addition, a sustained release also refers to a reduction in the burst of agent typically seen in first two hours following administration, and more preferably in the first hour, often referred to as the initial burst. In a preferred embodiment, the sustained release is characterized by both the period of release being longer in addition to a decreased burst. For example, a sustained release of insulin can be a release showing elevated levels out to at least 4 hours post administration, such as about 6 hours or more.

"Pulmonary delivery", as that term is used herein refers to delivery to the respiratory tract. The "respiratory tract", as defined herein, encompasses the upper airways, including the oropharynx and larynx, followed by the lower airways, which include the trachea followed by bifurcations into the bronchi and bronchioli (e.g., terminal and respiratory). The upper and lower airways are called the conducting airways. The terminal bronchioli then divide into respiratory bronchioli which then lead to the ultimate respiratory zone, namely, the alveoli, or deep lung. The deep lung, or alveoli, are typically the desired the target of inhaled therapeutic formulations for systemic drug delivery.

In one embodiment, the therapeutic, prophylactic or diagnostic agent and the oppositely charged lipid can be in association primarily as a result of ionic bonding, for example, ionic complexation. In another embodiment, the therapeutic, prophylactic or diagnostic agent and the oppositely charged lipid can be in association primarily as a result of hydrogen bonding. It is understood that a combination of ionic and hydrogen bonding can contribute to the association of the bioactive and charged lipid.

Ionic bonding is bonding which occurs via charge/charge interactions between atoms or groups of atoms. Since opposite charges attract, the atoms in an ionic compound are held together by this attraction.

Hydrogen bonding refers to bonding wherein a hydrogen atom is shared between two molecules. For example, a hydrogen atom covalently attached to an electronegative atom such as nitrogen, oxygen, sulfur or phosphorous shares its partial positive charge with a second electronegative atom, for example, nitrogen, oxygen, sulfur or phosphorous.

The particles suitable for use in the method can comprise a therapeutic, prophylactic or diagnostic agent in association with a charged lipid having a charge opposite to that of the agent upon association, prior to administration. In a preferred embodiment, the charges possessed by the agent and lipid, upon association, are the same as the charges which the agent and lipid possess at pulmonary pH following administration.

For example, the particles suitable for pulmonary delivery can comprise a therapeutic, prophylactic or diagnostic agent which possesses an overall net negative charge in association with a lipid which possesses an overall net positive charge. For example, the agent can be insulin and the lipid can be an ethylphosphatidylcholine, such as 1,2-dipalmitoyl-sn-glycero-3-ethylphosphatidylcholine (DPePC).

Alternatively, the particles suitable for pulmonary delivery can comprise a therapeutic, prophylactic or diagnostic agent which possesses an overall net positive charge in association with a lipid which possesses an overall net negative charge, preferably in the pulmonary pH range. For example, the agent can be albuterol sulfate which possesses an overall positive charge and the lipid can be 1,2-dipalmitoyl-sn-glycero- 3-[phospho-rac-(1-glycerol)] (DPPG) which possesses an overall net negative charge.

Further, the particles suitable for pulmonary delivery can comprise a therapeutic, prophylactic or diagnostic agent which has an overall net charge which can be modified by adjusting the pH of a solution of the agent prior to association with the charged lipid. For example, at a pH of about 7.4 insulin has an overall net charge which is negative. Therefore, insulin and a positively charged lipid can be associated at this pH, prior to administration, to prepare a particle having an bioactive agent in association with a charged lipid wherein the charged lipid has a charge opposite to that of the agent upon association. However, insulin can also be modified when in solution to possess an overall net charge which is positive by modifying the pH of the solution to be less than the pI of insulin (pI=5.5). As such, when insulin is in solution at a pH of 4, for example, it will possess an overall net charge which is positive. As this is the case, the positively charged insulin can be associated with a negatively charged lipid, for example, 1,2-distearoyl-sn-glycero-3-[phospho-rac-(1-glycerol)] (DSPG). Modification of the charge of the therapeutic, prophylactic or diagnostic agent is applicable to many agents, particularly, proteins.

"Pulmonary pH range", as that term is used herein, refers to the pH range which can be encountered in the lung of a patient. Typically, in humans, this range of pH is from about 6.4 to about 7.0, such as from 6.4 to about 6.7. pH values of the airway lining fluid (ALF) have been reported in "Comparative Biology of the Normal Lung", CRC Press, (1991) by R. A. Parent and range from 6.44 to 6.74)

"Charged lipid" as that term is used herein, refers to lipids which are capable of possessing an overall net charge. The charge on the lipid can be negative or positive. The lipid can be chosen to have a charge opposite to that of the active agent when the lipid and active agent are associated. In a preferred embodiment the charged lipid is a charged phospholipid. Preferably, the phospholipid is endogenous to the lung or can be metabolized upon administration to a lung endogenous phospholipid. Combinations of charged lipids can be used. The combination of charged lipid also has an overall net charge opposite to that of the bioactive agent upon association.

The charged phospholipid can be a negatively charged lipid such as, a 1,2-diacyl-sn-glycero-3-[phospho-rac-(1-glycerol)] and a 1,2-diacyl-sn-glycerol-3-phosphate.

The 1,2-diacyl-sn-glycero-3-[phospho-rac-(1-glycerol)] phospholipids can be represented by the Formula I:

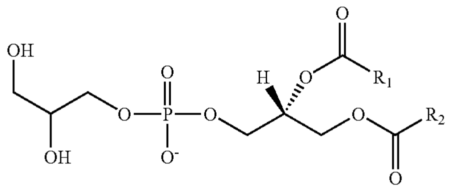

wherein $R_1$ and $R_2$ are independently aliphatic groups having from about 3 to about 24 carbon atoms, preferably from about 10 to about 20 carbon atoms.

Aliphatic group as that term is used herein in Formulas I–VI refers to substituted or unsubstituted straight chained, branched or cyclic $C_1$–$C_{24}$ hydrocarbons which can be completely saturated, which can contain one or more heteroatoms such as nitrogen, oxygen or sulfur and/or which can contain one or more units of unsaturation.

Suitable substituents on an aliphatic group include —OH, halogen (—Br, —Cl, —I and —F) —O(aliphatic, substituted), —CN, —$NO_2$, —COOH, —$NH_2$, —NH(aliphatic group, substituted aliphatic), —N(aliphatic group, substituted aliphatic group)$_2$, —COO(aliphatic group, substituted aliphatic group), —$CONH_2$, —CONH(aliphatic, substituted aliphatic group), —SH, —S(aliphatic, substituted aliphatic group) and —NH—C(═NH)—$NH_2$. A substituted aliphatic group can also have a benzyl, substituted benzyl, aryl (e.g., phenyl, naphthyl or pyridyl) or substituted aryl group as a substituent. A substituted aliphatic can have one or more substituents.

Specific examples of this type of negatively charged phospholipid include, but are not limited to, 1,2-distearoyl-sn-glycero-3-[phospho-rac-(1-glycerol)] (DSPG), 1,2-dimyristoyl-sn-glycero-3-[phospho-rac-(1-glycerol)] (DMPG), 1,2-dipalmitoyl-sn-glycero-3-phospho-rac-(1-glycerol)] (DPPG), 1,2-dilauroyl-sn-glycero-3-[phospho-rac-(1-glycerol)] (DLPG), and 1,2-dioleoyl-sn-glycero-3-[phospho-rac-(1-glycerol)] (DOPG).

The 1,2-diacyl-sn-glycerol-3-phosphate phospholipids can be represented by the Formula II:

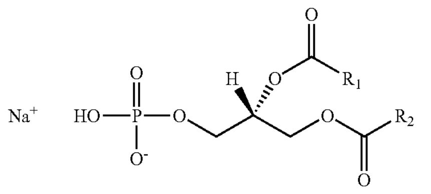

$R_1$ and $R_2$ are independently an aliphatic group having from about 3 to about 24 carbon atoms, preferably from about 10 to about 20 carbon atoms.

Specific examples of this type of phospholipid include, but are not limited to, 1,2-dimyristoyl-sn-glycero-3-phosphate (DMPA), 1,2-dipalmitoyl-sn-glycero-3-phosphate (DPPA), 1,2-dioleoyl-sn-glycero-3-phosphate (DOPA), 1,2-distearoyl-sn-glycero-3-phosphate (DSPA), and 1,2-dilauroyl-sn-glycero-3-phosphate (DLPA).

The charged lipid can be a positively charged lipid such as a 1,2-diacyl-sn-glycero-3-alkylphosphocholine, such as 1,2-diacyl-sn-glycero-3-ethylphosphocholine and a 1,2-diacyl-sn-glycero-3-alkylphosphoalkanolamine, such as 1,2-diacyl-sn-glycero-3-alkylphosphoethanolamine.

The 1,2-diacyl-sn-glycero-3-alkylphosphocholine phospholipids can be represented by the Formula III:

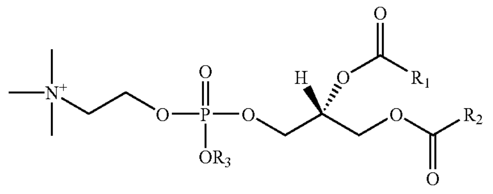

wherein $R_1$ and $R_2$ are independently an aliphatic group having from about 3 to about 24 carbon atoms, preferably from about 10 to about 20 carbon atoms. $R_3$ is an aliphatic group having from about 1 to about 24 carbons, for example, methyl, ethyl, propyl, butyl, pentyl, hexyl, heptyl, octyl and the like.

Specific examples of this type of positively charged phospholipid include, but are not limited to, 1,2-dipalmitoyl-sn-glycero-3-ethylphosphocholine(DPePC), 1,2-dimyristoyl-sn-glycero-3-ethylphosphocholine(DMePC), 1,2-distearoyl-sn-glycero-3-ethylphosphocholine(DSePC), 1,2-dilauroyl-sn-glycero-3-ethylphosphocholine (DLePC), and 1,2-dioleoyl-sn-glycero-3-ethylphosphocholine(DOePC).

The 1,2-diacyl-sn-glycero-3-alkylphosphoalkanolamine phospholipids can be represented by the Formula IV:

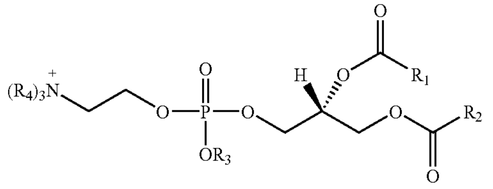

wherein $R_1$ and $R_2$ are independently an aliphatic group having from about 3 to about 24 carbon atoms, preferably from about 10 to about 20 carbon atoms. $R_3$ is an aliphatic group having from about 1 to about 24 carbons, for example, methyl, ethyl, propyl, butyl, pentyl, hexyl, heptyl, octyl and the like. $R_4$ is independently hydrogen, or an aliphatic group having from about 1 to about 6 carbon atoms.

Specific examples of this type of positively charged phospholipid include, but are not limited to, 1,2-dipalmitoyl-sn-glycero-3-ethylethanolamine(DPePE), 1,2-dimyristoyl-sn-glycero-3-ethylphosphoethanolamine(DMePE), 1,2-distearoyl-sn-glycero-3-ethylphosphoethanolamine(DSePE), 1,2-dilauroyl-sn-glycero-3-ethylphosphoethanolamine (DLePE), and 1,2-dioleoyl-sn-glycero-3-ethylphosphoethanolamine (DOePE).

Other charged lipids suitable for use in the invention include those described in U.S. Pat. No. 5,466,841 to Horrobin et al. issued on Nov. 14, 1995, U.S. Pat. Nos. 5,698,721 and 5,902,802 to Heath issued Dec. 16, 1997 and May 11, 1999, respectively, and U.S. Pat. No. 4,480,041 to Myles et al. issued Oct. 30, 1984, the entire contents of all of which are incorporated herein by reference.

The charged lipid and the therapeutic, prophylactic or diagnostic agent can be present in the particles of the invention at a charge ratio of lipid to active of from about 0.25:1 or more, preferably from about 0.25:1 to about 1:0.25, for example, about 0.5:1 to about 1:0.5. Preferably the charge ratio is about 1:1. When an excess of charge is present, it is preferred that the excess charge is contributed by the lipid.

A suitable charge ratio can be determined as follows. First, the number of charges present on both the bioactive agent and lipid, at the conditions under which association of the two will occur, prior to administration, should be determined. Next, the equivalent weight of both the bioactive agent and lipid should be determined. This can be carried out following the example below employing insulin as the bioactive agent and DPePC as the charged lipid at a pH of about 7.4.

| | |
|---|---|
| Molecular Weight of Insulin: | 5,800 g/mole |
| Number of Negative Charges on Insulin: | 6 equivalent |
| Equivalent Weight Per Charge: | 5,800 × 1/6 = 967 g |
| Molecular Weight of DPePC: | 763 g/mole |
| Number of Negative Charges on DPePC: | 1 equivalent |
| Equivalent Weight Per Charge: | 763 × 1/1 = 763 g |

Therefore, to obtain for example, a 1:1 charge ratio of DPePC to insulin 763 g DPePC is associated with 967 g insulin OR 1 g DPePC is associated with 1.27 (967/763=1.27) g insulin.

Alternatively, 967 g insulin is associated with 763 g DPePC OR 1 g insulin is associated with 0.79 (763/967=0.79) g DPePC.

In molar terms, 1 mole DPePC is associated with ⅙ mole insulin OR 1 mole insulin is associated with 6 moles DPePC.

This analysis can be used to determine the amount of lipid and active agent needed for any ratio desired and any combination of bioactive agent and lipid.

The charged lipid can be present in the particles in an amount ranging from about 1 to about 99% by weight. Preferably, the charged lipid is present in the particles in an amount ranging from about 10% to about 90% by weight.

The particles of the invention can also comprise phospholipids, which are zwitterionic and therefore do not possess an overall net charge. Such lipids, can assist in providing particles with the proper characterisitics for inhalation. Such phospholipids suitable for use in the invention include, but are not limited to, a 1,2-diacyl-sn-glycero-3-phosphocholine and a 1,2-diacyl-sn-glycero-3-phosphoethanolamine. These lipids can preferably be present in the particles in an amount ranging from about 10% to about 90% by weight. Preferably, these lipids can be present in the particles in an amount ranging from abut 50% to about 80% by weight.

The 1,2-diacyl-sn-glycero-3-phosphocholine phospholipids can be represented by Formula V:

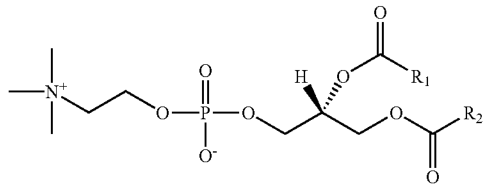

$R_1$ and $R_2$ are independently an aliphatic group having from about 3 to about 24 carbon atoms, preferably from about 10 to about 20 carbon atoms.

Specific examples of 1,2-diacyl-sn-glycero-3-phosphocholine phospholipids include, but are not limited to, 1,2-dipalmitoyl-sn-glycero-3-phosphocholine (DPPC), 1,2-distearoyl-sn-glycero-3-phosphocholine (DSPC), 1,2-dilaureoyl-sn-3-glycero-phosphocholine (DLPC), 1,2-dimyristoyl-sn-glycero-3-phosphocholine (DMPC), 1,2-dioleoyl-sn-glycero-3-phosphocholine (DOPC), The 1,2-diacyl-sn-glycero-3-phosphoalkanolamine phospholipids can be represented by Formula VI:

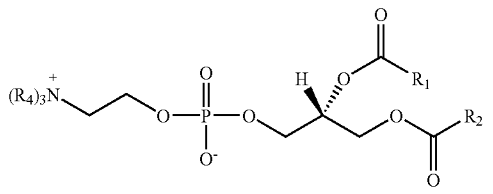

wherein $R_1$ and $R_2$ are independently an aliphatic group having from about 3 to about 24 carbon atoms, preferably, from about 10 to about 20 carbon atoms and $R_4$ is independently hydrogen or an aliphatic group having from about 1 to about 6 carbon atoms.

Specific examples of this type of phospholipid include, but are not limited to, 1,2-dipalmitoyl-sn-glycero-3-ethanolamine(DPPE), 1,2-dimyristoyl-sn-glycero-3-phosphoethanolamine(DMPE), 1,2-distearoyl-sn-glycero-3-phosphoethanolamine(DSPE), 1,2-dilauroyl-sn-glycero-3-phosphoethanolamine (DLPE), and 1,2-dioleoyl-sn-glycero-3-phosphoethanolamine (DOPE).

Therapeutic, prophylactic or diagnostic agents, can also be referred to herein as "bioactive agents", "medicaments" or "drugs". It is understood that one or more bioactive agents can be present in the particles of the invention. Hydrophilic as well as hydrophobic agents can be used. The agent must be capable of possessing an overall net charge. The amount of bioactive agent present in the particles of the invention can be from about 0.1 weight % to about 95 weight %, for example, from about 5 to about 75%, such as from about 10 to about 50%. Particles in which the drug is distributed throughout a particle are preferred.

Suitable bioactive agents include agents which can act locally, systemically or a combination thereof. The term "bioactive agent," as used herein, is an agent, or its pharmaceutically acceptable salt, which when released in vivo, possesses the desired biological activity, for example therapeutic, diagnostic and/or prophylactic properties in vivo.

Examples of bioactive agent include, but are not limited to, synthetic inorganic and organic compounds, proteins and peptides, polysaccharides and other sugars, lipids, and DNA and RNA nucleic acid sequences having therapeutic, prophylactic or diagnostic activities. Agents with a wide range of molecular weight can be used, for example, between 100 and 500,000 grams or more per mole.

The agents can have a variety of biological activities, such as vasoactive agents, neuroactive agents, hormones, anticoagulants, immunomodulating agents, cytotoxic agents, prophylactic agents, antibiotics, antivirals, antisense, antigens, antineoplastic agents and antibodies.

Proteins, include complete proteins, muteins and active fragments thereof, such as insulin, immunoglobulins, antibodies, cytokines (e.g., lymphokines, monokines, chemokines), interleukins, interferons (β-IFN, α-IFN and γ-IFN), erythropoietin, nucleases, tumor necrosis factor, colony stimulating factors, enzymes (e.g. superoxide dismutase, tissue plasminogen activator), tumor suppressors, blood proteins, hormones and hormone analogs (e.g., growth hormone, adrenocorticotropic hormone and luteinizing hormone releasing hormone (LHRH)), vaccines (e.g., tumoral, bacterial and viral antigens), antigens, blood coagulation factors; growth factors; granulocyte colony-stimulating factor ("G-CSF"); peptides include protein inhibitors, protein antagonists, and protein agonists, calcitonin; nucleic acids include, for example, antisense molecules, oligonucleotides, and ribozymes. Polysaccharides, such as heparin, can also be administered.

Bioactive agent for local delivery within the lung, include such as agents as those for the treatment of asthma, chronic obstructive pulmonary disease (COPD), emphysema, or cystic fibrosis. For example, genes for the treatment of diseases such as cystic fibrosis can be administered, as can beta agonists steroids, anticholinergics, and leukotriene modifers for asthma.

Other specific bioactive agents include, estrone sulfate, albuterol sulfate, parathyroid hormone-related peptide, somatostatin, nicotine, clonidine, salicylate, cromolyn sodium, salmeterol, formeterol, L-dopa, Carbidopa or a combination thereof, gabapenatin, clorazepate, carbamazepine and diazepam.

Nucleic acid sequences include genes, antisense molecules which can, for instance, bind to complementary DNA to inhibit transcription, and ribozymes.

The particles can include any of a variety of diagnostic agents to locally or systemically deliver the agents following administration to a patient. For example, imaging agents which include commercially available agents used in positron emission tomography (PET), computer assisted tomography (CAT), single photon emission computerized tomography, x-ray, fluoroscopy, and magnetic resonance imaging (MRI) can be employed.

Examples of suitable materials for use as contrast agents in MRI include the gadolinium chelates currently available, such as diethylene triamine pentacetic acid (DTPA) and gadopentotate dimeglumine, as well as iron, magnesium, manganese, copper and chromium.

Examples of materials useful for CAT and x-rays include iodine based materials for intravenous administration, such as ionic monomers typified by diatrizoate and iothalamate and ionic dimers, for example, ioxagalte.

Diagnostic agents can be detected using standard techniques available in the art and commercially available equipment.

The particles can further comprise a carboxylic acid which is distinct from the agent and lipid. In one embodiment, the carboxylic acid includes at least two carboxyl groups. Carboxylic acids, include the salts thereof as well as combinations of two or more carboxylic acids and/or salts thereof. In a preferred embodiment, the carboxylic acid is a hydrophilic carboxylic acid or salt thereof. Suitable carboxylic acids include but are not limited to hydroxydicarboxylic acids, hydroxytricarboxilic acids and the like. Citric acid and citrates, such as, for example sodium citrate, are preferred. Combinations or mixtures of carboxylic acids and/or their salts also can be employed.

The carboxylic acid can be present in the particles in an amount ranging from about 0 to about 80% weight. Preferably, the carboxylic acid can be present in the particles in an amount of about 10 to about 20%.

The particles suitable for use in the invention can further comprise a multivalent salt or its ionic components. As used herein, a "multivalent" salt refers to salts having a ionic component with a valency greater than one. For example, divalent salts. In a preferred embodiment, the salt is a divalent salt. In another preferred embodiment, the salt is a salt of an alkaline-earth metal, such as, for example, calcium chloride. The particles of the invention can also include mixtures or combinations of salts and/or their ionic components.

The salt or its ionic components are present in the particles in an amount ranging from about 0 to about 40% weight.

The particles suitable for use in the invention can further comprise an amino acid. In a preferred embodiment the amino acid is hydrophobic. Suitable naturally occurring hydrophobic amino acids, include but are not limited to, leucine, isoleucine, alanine, valine, phenylalanine, glycine and tryptophan. Combinations of hydrophobic amino acids can also be employed Non-naturally occurring amino acids include, for example, beta-amino acids. Both D, L configurations and racemic mixtures of hydrophobic amino acids can be employed. Suitable hydrophobic amino acids can also include amino acid derivatives or analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1–C8 hydrocarbons which are completely saturated, which contain one or two heteroatoms such as nitrogen, oxygen or sulfur and/or which contain one or more units of unsaturation. Aromatic or aryl groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F) —O(aliphatic, substituted aliphatic, benzyl, substituted benzyl, aryl or substituted aryl group), —CN, $—NO_2$, —COOH, $—NH_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO (aliphatic group, substituted aliphatic, benzyl, substituted benzyl, aryl or substituted aryl group), $—CONH_2$, —CONH (aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and $—NH—C(=NH)—NH_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acids analogs and salts thereof can be obtained commercially. Others can be synthesized by methods known in the art. Synthetic techniques are described, for example, in Green and Wuts, "*Protecting Groups in Organic Synthesis*", John Wiley and Sons, Chapters 5 and 7, 1991.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale has a value greater or equal to 0.5, in other words, has a tendency to partition in the nonpolar acid which is at least equal to that of glycine.

Examples of amino acids which can be employed include, but are not limited to: glycine, proline, alanine, cysteine, methionine, valine, leucine, tyrosine, isoleucine, phenylalanine, tryptophan. Preferred hydrophobic amino acids include leucine, isoleucine, alanine, valine, phenylalanine, glycine and tryptophan. Combinations of hydrophobic amino acids can also be employed. Furthermore, combinations of hydrophobic and hydrophilic (preferentially partitioning in water) amino acids, where the overall combination is hydrophobic, can also be employed. Combinations of one or more amino acids can also be employed.

The amino acid can be present in the particles of the invention in an amount from about 0% to about 60 weight %. Preferably, the amino acid can be present in the particles in an amount ranging from about 5 to about 30 weight %. The salt of a hydrophobic amino acid can be present in the particles of the invention in an amount of from about 0% to about 60 weight %. Preferably, the amino acid salt is present in the particles in an amount ranging from about 5 to about 30 weight %. Methods of forming and delivering particles which include an amino acid are described in U.S. patent application Ser. No. 09/382,959, filed on Aug. 25, 1999, entitled Use of Simple Amino Acids to Form Porous Particles During Spray Drying the entire teaching of which is incorporated herein by reference.

In a further embodiment, the particles can also include other materials such as, for example, buffer salts, dextran, polysaccharides, lactose, trehalose, cyclodextrins, proteins, peptides, polypeptides, fatty acids, fatty acid esters, inorganic compounds, phosphates.

In one embodiment of the invention, the particles can further comprise polymers. The use of polymers can further prolong release. Biocompatible or biodegradable polymers are preferred. Such polymers are described, for example, in U.S. Pat. No. 5,874,064, issued on Feb. 23, 1999 to Edwards et al., the teachings of which are incorporated herein by reference in their entirety.

In yet another embodiment, the particles include a surfactant other than one of the charged lipids described above. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

Suitable surfactants which can be employed in fabricating the particles of the invention include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxomer; a sorbitan fatty acid ester such as sorbitan trioleate (Span 85); and tyloxapol.

The surfactant can be present in the particles in an amount ranging from about 0 to about 60 weight %. Preferably, it can be present in the particles in an amount ranging from about 5 to about 50 weight %.

It is understood that when the particles includes a carboxylic acid, a multivalent salt, an amino acid, a surfactant or any combination thereof that interaction between these components of the particle and the charged lipid can occur.

The particles, also referred to herein as powder, can be in the form of a dry powder suitable for inhalation. In a particular embodiment, the particles can have a tap density of less than about 0.4 g/cm$^3$. Particles which have a tap density of less than about 0.4 g/cm$^3$ are referred to herein as "aerodynamically light particles". More preferred are particles having a tap density less than about 0.1 g/cm$^3$.

Aerodynamically light particles have a preferred size, e.g., a volume median geometric diameter (VMGD) of at least about 5 microns (μm). In one embodiment, the VMGD is from about 5 μm to about 30 μm. In another embodiment of the invention, the particles have a VMGD ranging from about 9 μm to about 30 μm. In other embodiments, the particles have a median diameter, mass median diameter (MMD), a mass median envelope diameter (MMED) or a mass median geometric diameter (MMGD) of at least 5 μm, for example from about 5 μm to about 30 μm.

Aerodynamically light particles preferably have "mass median aerodynamic diameter" (MMAD), also referred to herein as "aerodynamic diameter", between about 1 μm and about 5 μm. In one embodiment of the invention, the MMAD is between about 1 μm and about 3 μm. In another embodiment, the MMAD is between about 3 μm and about 5 μm.

In another embodiment of the invention, the particles have an envelope mass density, also referred to herein as "mass density" of less than about 0.4 g/cm$^3$. The envelope mass density of an isotropic particle is defined as the mass of the particle divided by the minimum sphere envelope volume within which it can be enclosed.

Tap density can be measured by using instruments known to those skilled in the art such as the Dual Platform Microprocessor Controlled Tap Density Tester (Vankel, N.C.) or a GeoPyc™ instrument (Micrometrics Instrument Corp., Norcross, Ga. 30093). Tap density is a standard measure of the envelope mass density. Tap density can be determined using the method of USP Bulk Density and Tapped Density, United States Pharmacopia convention, Rockville, Md., 10$^{th}$ Supplement, 4950–4951, 1999. Features which can contribute to low tap density include irregular surface texture and porous structure.

The diameter of the particles, for example, their VMGD, can be measured using an electrical zone sensing instrument such as a Multisizer IIe, (Coulter Electronic, Luton, Beds, England), or a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition within targeted sites within the respiratory tract.

Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid impinger (MSLI).

The aerodynamic diameter, $d_{aer}$, can be calculated from the equation:

$$d_{aer}=d_g\sqrt{\rho_{tap}}$$

where $d_g$ is the geometric diameter, for example the MMGD and ρ is the powder density.

Particles which have a tap density less than about 0.4 g/cm$^3$, median diameters of at least about 5 μm, and an aerodynamic diameter of between about 1 μm and about 5 μm, preferably between about 1 μm and about 3 μm, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those currently used for inhalation therapies.

In comparison to smaller particles the larger aerodynamically light particles, preferably having a VMGD of at least about 5 μm, also can potentially more successfully avoid phagocytic engulfinent by alveolar macrophages and clearance from the lungs, due to size exclusion of the particles from the phagocytes' cytosolic space. Phagocytosis of particles by alveolar macrophages diminishes precipitously as particle diameter increases beyond about 3 μm. Kawaguchi, H., et al., *Biomaterials* 7: 61–66 (1986); Krenis, L. J. and Strauss, B., *Proc. Soc. Exp. Med.,* 107: 748–750 (1961); and Rudt, S. and Muller, R. H., *J. Contr. Rel.,* 22: 263–272 (1992). For particles of statistically isotropic shape, such as spheres with rough surfaces, the particle envelope volume is approximately equivalent to the volume of cytosolic space required within a macrophage for complete particle phagocytosis.

The particles may be fabricated with the appropriate material, surface roughness, diameter and tap density for localized delivery to selected regions of the respiratory tract such as the deep lung or upper or central airways. For example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to about 5 μm are preferred for delivery to the central and upper airways. Particles having an aerodynamic diameter ranging from about 1 to about 3 μm are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.,* 26: 293–317(1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 μm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K.K. Midha), pp. 95–117, Stuttgart: Medpharm Scientific Publishers, 1992)), by the formula:

$$d_{aer}=d\sqrt{\rho}$$

where the envelope mass ρ is in units of g/cm$^3$. Maximal deposition of monodispersed aerosol particles in the alveolar region of the human lung (~60%) occurs for an aerodynamic diameter of approximately $d_{aer}$=3 μm. Heyder, J. et al., *J. Aerosol Sci.,* 17: 811–825 (1986). Due to their small envelope mass density, the actual diameter d of aerodynamically light particles comprising a monodisperse inhaled powder that will exhibit maximum deep-lung deposition is:

$$d=3/\sqrt{\rho}\ \mu m \text{ (where } \rho<1 \text{ g/cm}^3\text{);}$$

where d is always greater than 3 μm. For example, aerodynamically light particles that display an envelope mass density, ρ=0.1 g/cm$^3$, will exhibit a maximum deposition for particles having envelope diameters as large as 9.5 μm. The increased particle size diminishes interparticle adhesion forces. Visser, J., *Powder Technology,* 58: 1–10. Thus, large particle size increases efficiency of aerosolization to the deep lung for particles of low envelope mass density, in addition to contributing to lower phagocytic losses.

The aerodyanamic diameter can be calculated to provide for maximum deposition within the lungs, previously achieved by the use of very small particles of less than about five microns in diameter, preferably between about one and about three microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

Suitable particles can be fabricated or separated, for example by filtration or centrifugation, to provide a particle sample with a preselected size distribution. For example, greater than about 30%, 50%, 70%, or 80% of the particles in a sample can have a diameter within a selected range of at least about 5 μm. The selected range within which a certain percentage of the particles must fall may be for example, between about 5 and about 30 μm, or optimally between about 5 and about 15 μm. In one preferred embodiment, at least a portion of the particles have a diameter between about 9 and about 11 μm. Optionally, the particle sample also can be fabricated wherein at least about 90%, or optionally about 95% or about 99%, have a diameter within the selected range. The presence of the higher proportion of the aerodynamically light, larger diameter particles in the particle sample enhances the delivery of therapeutic or diagnostic agents incorporated therein to the deep lung. Large diameter particles generally mean particles having a median geometric diameter of at least about 5 μm.

The particles can be prepared by spray drying. For example, a spray drying mixture, also referred to herein as "feed solution" or "feed mixture", which includes the bioactive agent and one or more charged lipids having a charge opposite to that of the active agent upon association are fed to a spray dryer.

For example, when employing a protein active agent, the agent may be dissolved in a buffer system above or below the pIof the agent. Specifically, insulin for example may be dissolved in an aqueous buffer system (e.g., citrate, phosphate, acetate, etc.) or in 0.01 N HCl. The pH of the resultant solution then can be adjusted to a desired value using an appropriate base solution (e.g., 1 N NaOH). In one preferred embodiment, the pH may be adjusted to about pH 7.4. At this pH insulin molecules have a net negative charge (pI=5.5). In another embodiment, the pH may be adjusted to about pH 4.0. At this pH insulin molecules have a net positive charge (pI=5.5). Typically the cationic phospholipid is dissolved in an organic solvent or combination of solvents. The two solutions are then mixed together and the resulting mixture is spray dried.

For a small molecule active agent, the agent may be dissolved in a buffer system above or below the pKa of the ionizable group(s). Specifically, albuterol sulfate or estrone sulfate, for example, can be dissolved in an aqueous buffer system (e.g., citrate, phosphate, acetate, etc.) or in sterile water for irrigation. The pH of the resultant solution then can be adjusted to a desired value using an appropriate acid or base solution. If the pH is adjusted to about pH 3 to about pH 8 range, estrone sulfate will possess one negative charge per molecule and albuterol sulfate will possess one positive charge per molecule. Therefore, charge interaction can be engineered by the choice of an appropriate phospholipid. Typically the negatively charged or the positively charged phospholipid is dissolved in an organic solvent or combination of solvents and the two solutions are then mixed together and the resulting mixture is spray dried.

Suitable organic solvents that can be present in the mixture being spray dried include, but are not limited to, alcohols for example, ethanol, methanol, propanol, isopropanol, butanols, and others. Other organic solvents include, but are not limited to, perfluorocarbons, dichloromethane, chloroform, ether, ethyl acetate, methyl tert-butyl ether and others. Aqueous solvents that can be present in the feed mixture include water and buffered solutions. Both organic and aqueous solvents can be present in the spray-drying mixture fed to the spray dryer. In one embodiment, an ethanol water solvent is preferred with the ethanol:water ratio ranging from about 50:50 to about 90:10. The mixture can have a, acidic or alkaline pH. Optionally, a pH buffer can be included. Preferably, the pH can range from about 3 to about 10.

The total amount of solvent or solvents being employed in the mixture being spray dried generally is greater than 99 weight percent. The amount of solids (drug, charged lipid and other ingredients) present in the mixture being spray dried generally is less than about 1.0 weight percent. Preferably, the amount of solids in the mixture being spray dried ranges from about 0.05% to about 0.5% by weight.

Using a mixture which includes an organic and an aqueous solvent in the spray drying process allows for the combination of hydrophilic and hydrophobic components, while not requiring the formation of liposomes or other structures or complexes to facilitate solubilization of the combination of such components within the particles.

Suitable spray-drying techniques are described, for example, by K. Masters in "Spray Drying Handbook", John Wiley & Sons, New York, 1984. Generally, during spray-drying, heat from a hot gas such as heated air or nitrogen is used to evaporate the solvent from droplets formed by atomizing a continuous liquid feed. Other spray-drying techniques are well known to those skilled in the art. In a preferred embodiment, a rotary atomizer is employed. An example of a suitable spray dryer using rotary atomization includes the Mobile Minor spray dryer, manufactured by Niro, Denmark. The hot gas can be, for example, air, nitrogen or argon.

Preferably, the particles of the invention are obtained by spray drying using an inlet temperature between about 100° C. and about 400° C. and an outlet temperature between about 50° C. and about 130° C.

The spray dried particles can be fabricated with a rough surface texture to reduce particle agglomeration and improve flowability of the powder. The spray-dried particle can be fabricated with features which enhance aerosolization via dry powder inhaler devices, and lead to lower deposition in the mouth, throat and inhaler device.

The particles of the invention can be employed in compositions suitable for drug delivery via the pulmonary system. For example, such compositions can include the particles and a pharmaceutically acceptable carrier for administration to a patient, preferably for administration via inhalation. The particles can be co-delivered with larger carrier particles, not including a therapeutic agent, the latter possessing mass median diameters for example in the range between about 50 μm and about 100 μm. The particles can be administered alone or in any appropriate pharmaceutically acceptable carrier, such as a liquid, for example saline, or a powder, for administration to the respiratory system.

Particles including a medicament, for example one or more of the drugs listed above, are administered to the respiratory tract of a patient in need of treatment, prophylaxis or diagnosis. Administration of particles to the respiratory system can be by means such as known in the art. For example, particles are delivered from an inhalation device. In a preferred embodiment, particles are administered via a dry powder inhaler (DPI). Metered-dose-inhalers (MDI), nebulizers or instillation techniques also can be employed.

Various suitable devices and methods of inhalation which can be used to administer particles to a patient's respiratory tract are known in the art. For example, suitable inhalers are described in U.S. Pat. No. 4,069,819, issued Aug. 5, 1976 to Valentini, et al., U.S. Pat. No.4,995,385 issued Febr. 26, 1991 to Valentini, et al., and U.S. Pat. No. 5,997,848 issued Dec. 7, 1999 to Patton, et al. Various suitable devices and methods of inhalation which can be used to administer particles to a patient's respiratory tract are known in the art. For example, suitable inhalers are described in U.S. Pat. Nos. 4,995,385, and 4,069,819 issued to Valentini, et al, U.S. Pat. No. 5,997,848 issued to Patton. Other examples include, but are not limited to, the Spinhaler® (Fisons, Loughborough, U.K.), Rotahaler® (Glaxo-Wellcome, Research Triangle Technology Park, North Carolina), FlowCaps® (Hovione, Loures, Portugal), Inhalator® (Boehringer-Ingelheim, Germany), and the Aerolizer® (Novartis, Switzerland), the diskhaler (Glaxo-Wellcome, RTP, NC) and others, such as known to those skilled in the art. Preferably, the particles are administered as a dry powder via a dry powder inhaler.

Preferably, particles administered to the respiratory tract travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. In a preferred embodiment of the invention, most of the mass of particles deposits in the deep lung. In another embodiment of the invention, delivery is primarily to the central airways. Delivery to the upper airways can also be obtained.

In one embodiment of the invention, delivery to the pulmonary system of particles is in a single, breath-actuated step, as described in U.S. Patent Application, High Efficient Delivery of a Large Therapeutic Mass Aerosol, application Ser. No. 09/591,307, filed Jun. 9, 2000, which is incorporated herein by reference in its entirety. In another embodiment of the invention, at least 50% of the mass of the particles stored in the inhaler receptacle is delivered to a subject's respiratory system in a single, breath-activated step. In a further embodiment, at least 5 milligrams and preferably at least 10 milligrams of a medicament is delivered by administering, in a single breath, to a subject's respiratory tract particles enclosed in the receptacle. Amounts as high as 15, 20, 25, 30, 35, 40 and 50 milligrams can be delivered.

As used herein, the term "effective amount" means the amount needed to achieve the desired therapeutic or diagnostic effect or efficacy. The actual effective amounts of drug can vary according to the specific drug or combination thereof being utilized, the particular composition formulated, the mode of administration, and the age, weight, condition of the patient, and severity of the symptoms or condition being treated. Dosages for a particular patient can be determined by one of ordinary skill in the art using conventional considerations, (e.g. by means of an appropriate, conventional pharmacological protocol). For example, effective amounts of albuterol sulfate range from about 100 micrograms (μg) to about 10 milligrams (mg).

Aerosol dosage, formulations and delivery systems also may be selected for a particular therapeutic application, as described, for example, in Gonda, I. "Aerosols for delivery of therapeutic and diagnostic agents to the respiratory tract," in *Critical Reviews in Therapeutic Drug Carrier Systems,* 6: 273–313, 1990; and in Moren, "Aerosol dosage forms and formulations," in: *Aerosols in Medicine. Principles, Diagnosis and Therapy,* Moren, et al., Eds, Esevier, Amsterdam, 1985.

Drug release rates can be described in terms of release constants. The first order release constant can be expressed using the following equations:

$$M_{(t)}=M_{(\infty)}*(1-e^{-k*t}) \quad (1)$$

Where k is the first order release constant. $M_{(\infty)}$ is the total mass of drug in the drug delivery system, e.g. the dry powder, and $M_{(t)}$ is the amount of drug mass released from dry powders at time t.

Equations (1) may be expressed either in amount (i.e., mass) of drug released or concentration of drug released in a specified volume of release medium. For example, Equation (1) may be expressed as:

$$C_{(t)}=C_{(\infty)}*(1-e^{-k*t}) \text{ or } Release_{(t)}=Release_{(\infty)}*(1-e^{-k*t}) \quad (2)$$

Where k is the first order release constant. $C_{(\infty)}$ is the maximum theoretical concentration of drug in the release medium, and $C_{(t)}$ is the concentration of drug being released from dry powders to the release medium at time t.

Drug release rates in terms of first order release constant can be calculated using the following equations:

$$k=-In(M_{(\infty)}-M_{(t)})/M_{(\infty)}/t \quad (3)$$

The release constants presented in Tables 4 and 8 employ equation (2).

As used herein, the term "a" or "an" refers to one or more.

The term "nominal dose" as used herein, refers to the total mass of bioactive agent which is present in the mass of particles targeted for administration and represents the maximum amount of bioactive agent available for administration.

Exemplification

Materials

Humulin L (human insulin zinc suspension) was obtained from Lilly (100 U/mL)

Mass Median Aerodynamic Diameter—MMAD (μm)

The mass median aerodynamic diameter was determined using an Aerosizer/Aerodisperser (Amherst Process Instrument, Amherst, Mass.). Approximately 2 mg of powder formulation was introduced into the Aerodisperser and the aerodynamic size was determined by time of flight measurements.

Volume Median Geometric Diameter—VMGD (μm)

The volume median geometric diameter was measured using a RODOS dry powder disperser (Sympatec, Princeton, N.J.) in conjunction with a HELOS laser diffractometer (Sympatec). Powder was introduced into the RODOS inlet and aerosolized by shear forces generated by a compressed air stream regulated at 2 bar. The aerosol cloud was subsequently drawn into the measuring zone of the HELOS, where it scattered light from a laser beam and produced a fraunhofer diffraction pattern used to infer the particle size distribution and determine the median value.

Where noted, the volume median geometric diameter was determined using a Coulter Multisizer II. Approximately 5–10 mg powder formulation was added to 50 mL isoton II solution until the coincidence of particles was between 5 and 8%.

Determination of Plasma Insulin Levels

Quantification of insulin in rat plasma was performed using a human insulin specific RIA kit (Linco Research, Inc., St. Charles, Mo., catalog #HI-14K). The assay shows less than 0.1% cross reactivity with rat insulin. The assay kit procedure was modified to accommodate the low plasma volumes obtained from rats, and had a sensitivity of approximately 5μU/mL.

Determination of Estrone—Sulfate Plasma Levels

Quantification of estrone-sulfate in rat plasma was performed using an estrone-sulfate RIA kit (Diagnostic Systems Laboratories, Inc., Webster, Tex., catalog #DSL-C5400). The assay kit procedure was modified to accommodate the low plasma volumes obtained from rats and to correct for influence of the human serum standard matrix, and had a sensitivity of approximately 0.025 ng/mL.

Preparation of Insulin Fommulations

The powder formulations listed in Table 1 were prepared as follows. Pre-spray drying solutions were prepared by dissolving the lipid in ethanol and the insulin, leucine, and/or sodium citrate in water. The ethanol solution was then mixed with the water solution at a ratio of 60/40 ethanol water. Final total solute concentration of the solution used for spray drying varied from 1 g/L to 3 g/L. As an example, the DPPC/citrate/insulin (60/10/30) spray drying solution was prepared by dissolving 600 mg DPPC in 600 mL of ethanol, dissolving 100 mg of sodium citrate and 300 mg of insulin in 400 mL of water and then mixing the two solutions to yield one liter of cosolvent with a total solute concentration of 1 g/L (w/v). Higher solute concentrations of 3 g/L (w/v) were prepared by dissolving three times more of each solute in the same volumes of ethanol and water.

The solution was then used to produce dry powders. A Nitro Atomizer Portable Spray Dryer (Niro, Inc., Columbus, Md.) was used. Compressed air with variable pressure (1 to 5 bar) ran a rotary atomizer (2,000 to 30,000 rpm) located above the dryer. Liquid feed with varying rate (20 to 66 mL/min) was pumped continuously by an electronic metering pump (LMI, Model #A151-192s) to the atomizer. Both the inlet and outlet temperatures were measured. The inlet temperature was controlled manually; it could be varied between 100° C. and 400° C. and was established at 100, 110, 150, 175 or 200° C., with a limit of control of 5° C. The outlet temperature was determined by the inlet temperature and such factors as the gas and liquid feed rates (it varied between 50° C. and 130° C.). A container was tightly attached to the cyclone for collecting the powder product.

TABLE 1

| POWDER FORMU- | COMPOSITION (%) | | | | | | |
|---|---|---|---|---|---|---|---|
| LATION NUMBER | DPePC | DSePC | DPPG | DPPC | Leu-cine | Citrate | Insu-lin |
| 1† | | | | 70 | 10 | | 20 |
| 2 | | 70 | | | 20 | | 10 |
| 3 | | 70 | | | 10 | | 20 |
| 4 | 50 | | | | | | 50 |
| 5 ‡ | | | 40 | | | 10 | 50 |
| 6 | 70 | | | | 10 | | 20 |
| 7 | 50 | | | | | | 50 |
| 8 | 54.5 | | | | | | 45.5 |

TABLE 1-continued

| POWDER FORMULATION NUMBER | COMPOSITION (%) DPePC | DSePC | DPPG | DPPC | Leucine | Citrate | Insulin |
|---|---|---|---|---|---|---|---|
| 9 | 50 | | | | 10 | | 40 |
| 10 | 70 | | | | 10 | | 2 |
| 11 | 70 | | | | 8 | 2 | 20 |
| 12† | | | | 40 | | 10 | 50 |
| 13† | | | | 60 | | 10 | 30 |
| 13A† | | | | 60 | | 10 | 30 |
| 14‡ | | | 70 | | 20 | | |
| 15† | | | | 70 | 20 | | 10 |

†Lots #4-xxx-201002 (#1), 4-XXX-201 065 (#12), 04-00024 (#13), 4-xxx-114068C (#13A) and 4-xxx-167113 (#15), which contain the lipid DPPC, serve as negative controls.
‡Powder formulation #5 was spray dried at pH = 4.0.
‡Powder formulation #14 was spray dried at pH = 7.4.

The physical characteristic of the insulin containing powders is set forth in Table 2. The MMAD and VMGD were determined as detailed above.

The nominal insulin dose administered was 100 μg per rat. To achieve the nominal doses, the total weight of powder administered per rat ranged from 0.2 mg to 1 mg, depending on percent composition of each powder. Male Sprague-Dawley rats were obtained from Taconic Farms (Germantown, N.Y.). At the time of use, the animals weighed 386 g in average (±5 g S.E.M.). The animals were allowed free access to food and water.

The powders were delivered to the lungs using an insufflator device for rats (PennCentury, Philadelphia, Pa.). The powder amount was transferred into the insufflator sample chamber. The delivery tube of the insufflator was then inserted through the mouth into the trachea and advanced until the tip of the tube was about a centimeter from the carina (first bifurcation). The volume of air used to deliver the powder from the insufflator sample chamber was 3 mL, delivered from a 10 mL syringe. In order to maximize powder delivery to the rat, the syringe was recharged and discharged two more times for a total of three air discharges per powder dose.

The injectable insulin formulation Humulin L was administered via subcutaneous injection, with an injection volume

TABLE 2

| Formulations | Compositions (% weight basis) | MMAD (μm)§ | VMGD (μm)¶ | Density (g/cc)‡ |
|---|---|---|---|---|
| Humulin R | — | — | — | — |
| Humulin L | — | — | — | — |
| Humulin U | — | — | — | — |
| 1 | DPPC/Leu/Insulin (Sigma) = 70/10/20 | 2.6 | 13.4 | 0.038 |
| 2 | DSePC (Avanti)/Leu/Insulin (Sigma) = 70/10/20 | 3.3 | 10.0 | 0.109 |
| 3 | DSePC (Avanti)/Leu/Insulin (Sigma) = 70/10/20 | 3.4 | 13.6 | 0.063 |
| 4 | DPePC (Avanti)/Insulin (Sigma) = 50/50 | 3.2 | 15.3 | 0.044 |
| 5 | DPPG/Sodium Citrate/Insulin = 40/10/50 | 3.9 | 11.6 | 0.113 |
| 6 | DPePC (Genzyme)/Leu/Insulin (BioBras) = 70/10/20 | 2.6 | 9.1 | 0.082 |
| 7 | DPePC (Avanti)/Insulin (BioBras)= 50/50 | 2.8 | 11.4 | 0.060 |
| 8 | DPePC (Genzyme)/Insulin (BioBras) = 54.5/45.5 | 2.8 | 12.6 | 0.049 |
| 9 | DPePC (Genzyme)/Leu/Insulin (BioBras) = 50/10/40 | 2.2 | 8.4 | 0.069 |
| 10 | DPePC (Avanti)/Leu/Insulin (BioBras) = 70/10/20 | 3.7 | 15.5 | 0.057 |
| 11 | DPePC (Avanti)/Leu/Sodium Citrate/Insulin (BioBras) = 70/8/2/20 | 2.6 | 15.3 | 0.029 |
| 12 | DPPC/Sodium Citrate/Insulin = 40/10/50 | 3.5 | 11.6 | 0.091 |
| 13 | DPPC/Insulin/Sodium Citrate = 60/30/10 | 1.9 | 8.0 | 0.056 |

†Used as a control formulation for comparison in either in vitro or in vivo studies.
§Mass median aerodynamic diameter
¶Volumetric median geometric diameter at 2 bar pressure
‡Determined using $d_{aer} = d_g\sqrt{\rho}$ The data presented in Table 2 showing the physical characteristics of the formulations comprising insulin are predictive of the respirability of the formulations. That is, as discussed above the large geometric diameters, small aerodynamic diameters and low densities possessed by the powder prepared as described herein render the particles respirable.

In Vivo Insulin Experiments

The following experiment was performed to determine the rate and extent of insulin absorption into the blood stream of rats following pulmonary administration of dry powder formulations comprising insulin to rats.

of 7.2 μL for a nominal dose of 25 μg insulin. Catheters were placed into the jugular veins of the rats the day prior to dosing. At sampling times, blood samples were drawn from the jugular vein catheters and immediately transferred to EDTA coated tubes. Sampling times were 0, 0.25, 0.5, 1, 2, 4, 6, 8, and 24 hrs. after powder administration. In some cases an additional sampling time (12 hrs.) was included, and/or the 24 hr. time point omitted. After centrifugation, plasma was collected from the blood samples. Plasma samples were stored at 4° C. if analysis was performed within 24 hours or at −75° C. if analysis would occur later than 24 hours after collection. The plasma insulin concentration was determined as described above.

Table 3 contains the insulin plasma levels quantified using the assay described above.

TABLE 3

| Time (hrs) | PLASMA INSULIN CONCENTRATION (μU/mL) ± S.E.M. 1 | 2 | 3 | 4 | 5 | 6 | 13A | 14 | Humlin L | 15 |
|---|---|---|---|---|---|---|---|---|---|---|
| 0 | 5.0± 0.0 | 5.2± 0.2 | 5.0± 0.0 | 5.0± 0.0 | 5.3± 0.2 | 5.7± 0.7 | 5.0± 0.0 | 5.0± 0.0 | 5.0± 0.0 | ±5.0± 0.0 |
| 0.25 | 1256.4± 144.3 | 61.6± 22.5 | 98.5± 25.3 | 518.2± 179.2 | 240.8± 67.6 | 206.8± 35.1 | 1097.7± 247.5 | 933.9 ± 259.7 | 269.1± 82.8 | 1101.9± 258.9 |
| 0.5 | 1335.8± 81.9 | 85.2± 21.7 | 136.7± 37.6 | 516.8± 190.9 | 326.2± 166.9 | 177.3± 7.8 | 893.5± 177.0 | 544.9 ± 221.1 | 459.9± 91.6 | 1005.4± 263.9 |
| 1 | 859.0± 199.4 | 85.4± 17.6 | 173.0± 28.8 | 497.0± 93.9 | 157.3± 52.5 | 170.5± 32.9 | 582.5± 286.3 | 229.6 ± 74.4 | 764.7± 178.8 | 387.5± 143.9 |
| 2 | 648.6± 171.1 | 94.8± 25.0 | 158.3± 39.1 | 496.5± 104.9 | 167.7± 70.5 | 182.2± 75.0 | 208.5± 78.3 | 129.8 ± 45.7 | 204.4± 36.7 | 343.8± 95.3 |
| 4 | 277.6± 86.8 | 52.5± 9.1 | 98.0± 24.3 | 343.8± 66.7 | 144.8± 43.8 | 170.2± 56.3 | 34.9± 5.4 | 41.9 ± 28.7 | 32.1± 22.6 | 170.6± 79.9 |
| 6 | 104.0± 43.1 | 33.0± 10.7 | 58.7± 4.1 | 251.2± 68.4 | 95.7± 27.3 | 159.5± 43.4 | 12.3± 2.4 | 9.0 ± 2.9 | 11.1± 7.5 | 15.4± 4.5 |
| 8 | 54.4± 34.7 | 30.2± 8.1 | 42.5± 17.8 | 63.2± 16.5 | 52.5± 13.7 | 94.8± 23.5 | 5.2± 0.1 | 5.0 ± 0.0 | 5.5± 2.1 | 6.5± 0.6 |
| 12 | | | | 17.2± 6.5 | | | | | | |
| 24 | | | | 5.0± 0.0 | 5.5± 0.3 | | | | | |
| n | 5 | 5 | 6 | 6 | 6 | 6 | | | 8 | |

The in vivo release data of Table 3 show that powder formulations comprising insulin and positively charged lipids (DPePC and DSePC) have significantly lower initial burst of insulin than that seen with powder formulations comprising insulin and the lipid DPPC (Formulations 1 and 13) and sustained elevated levels at 6 to 8 hours. FIG. 1 sets forth the release profile for insulin from Formulations 2, 3, 6 and 15.

Figure 2:
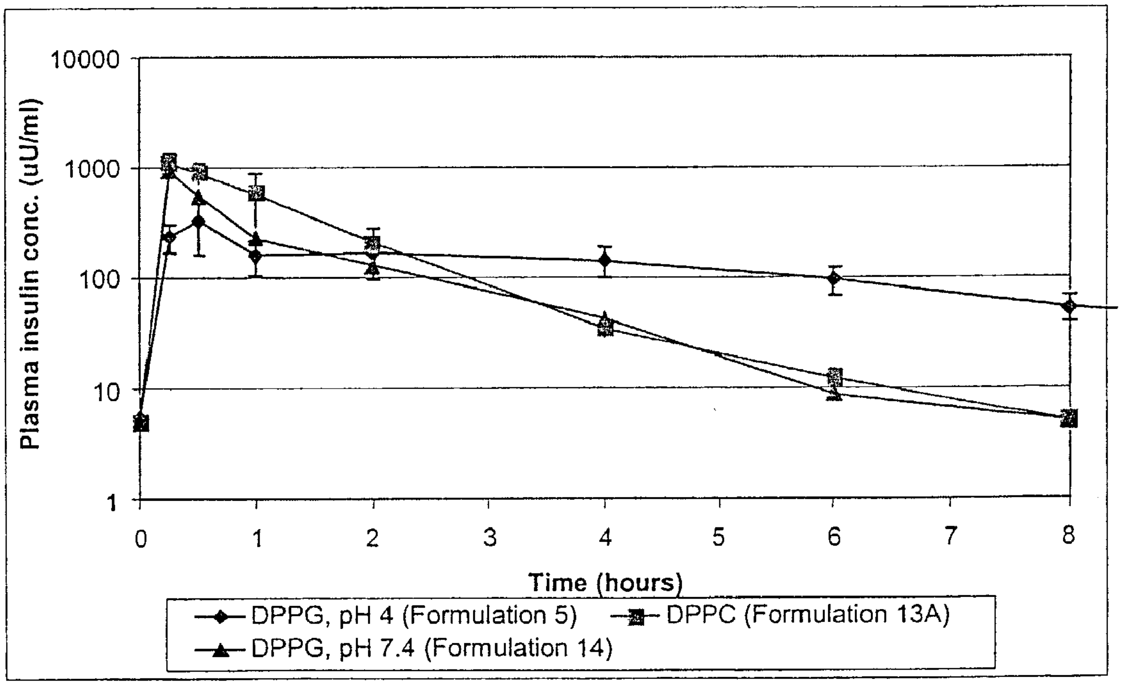
FIG. 2 is a graph of the in vivo release profile of dry powder formulations comprising insulin in combination with a lipid with no overall net charge (DPPC) or insulin in combination with a charged lipid having an overall negative charge (DPPG) and spray dried with the active agent at either pH 4 or 7.4.

In addition, the use of charged lipids having a charge which is the same of the active at neutral pH, can also be employed provided that the preparation of the spray dried formulation is conducted at a pH where the lipid and active agent possess overall charges which are opposite and are therefore capable of charge interaction. See, for example, Formulations 5 which employs the negatively charged lipid DPPG. Formulation 5 was prepared and spray dried at a pH of about 4.0. At this pH, DPPG is negatively charged and insulin becomes positively charged (pI=5.5) thereby providing for a charge interaction to occur. However, when the DPPG and insulin are prepared and spray dried at pH=7.4 where both the DPPG and insulin possess an overall negative charge, Formulation 14, the proper environment for charge interaction to occur is not provided. It is noted that Formulation 5 showed a significantly lower initial burst of insulin (240.8±67.6 μU/mL) as compared to Formulation 14 (933.9±259.7 μU/mL) with higher sustained levels at 6 to 8 hours post treatment. FIG. 2 shows a comparison of the in vivo release profile for Formulations 5, 14 and 13A (lipid, DPPC).

In Vitro Analysis of Insulin—Containing Formulations

The in vitro release of insulin containing dry powder formulations was performed as described by Gietz et al. in *Eur. J. Pharm. Biopharm.,* 45:259–264 (1998), with several modifications. Briefly, in 20 mL screw-capped glass scintillation vials about 10 mg of each dry powder formulation was mixed with 4 mL of warm (37° C.) 1% agarose solution using polystyrene stir bars. The resulting mixture was then distributed in 1 mL aliquots to a set of five fresh 20 mL glass scintillation vials. The dispersion of dry powder in agarose was cooled in an ambient temperature dessicator box protected from light to allow gelling. Release studies were conducted on an orbital shaker at about 37° C. At predetermined time points, previous release medium (1.5 mL) was removed and fresh release medium (1.5 mL) was added to each vial. Typical time points for these studies were 5 minutes, 1, 2, 4, 6 and 24 hours. The release medium used consisted of 20 mM 4-(2-hydroxyethyl)-piperazine-1-ethanesulfonic acid (HEPES), 138 mM NaCl, 0.5% Pluronic (Synperonic PE/F68; to prevent insulin fibrillation in the release medium); pH 7.4. A Pierce (Rockford, Ill.) protein assay kit (See *Anal Biochem,* 150:76–85 (1985)) using known concentrations of insulin standard was used to monitor insulin concentrations in the release medium.

Table 4 summarizes the in vitro release data and first order release constants for powder formulations of Table 1 comprising insulin.

TABLE 4

| Powder Formulation Number | Cumulative % Insulin Released at 6 hr | Cumulative % Insulin Released at 24 hr | Maximum‡ Release at 24 hr (Cumulative %) | First Order‡ Release Constants ($hr^{-1}$) |
|---|---|---|---|---|
| Humulin R | 92.67 ± 0.36 | 94.88 ± 0.22 | 91.6 ± 5.42 | 1.0105 ± 0.2602 |
| Humulin L | 19.43 ± 0.41 | 29.71 ± 0.28 | 36.7 ± 2.56 | 0.0924 ± 0.0183 |
| Humulin U | 5.17 ± 0.18 | 12.65 ± 0.43 | 46.6 ± 27.0 | 0.0158 ± 0.0127 |
| 2 | 31.50 ± 0.33 | 47.52 ± 0.43 | 48.22 ± 0.46 | 0.1749 ± 0.0038 |
| 3 | 26.34 ± 0.71 | 37.49 0.27 | 38.08 ± 0.72 | 0.1837 ± 0.0079 |
| 4 | 24.66 ± 0.20 | 31.58 ± 0.33 | 31.51 ± 1.14 | 0.2457 ± 0.0214 |
| 5 | 29.75 ± 0.17 | 35.28 ± 0.19 | 33.66 ± 2.48 | 0.4130 ± 0.0878 |
| 6 | 17.04 ± 0.71 | 24.71 ± 0.81 | 25.19 ± 0.52 | 0.1767 ± 0.0083 |
| 7 | 13.53 ± 0.19 | 19.12 ± 0.40 | 19.51 ± 0.48 | 0.1788 ± 0.0101 |
| 8 | 13.97 ± 0.27 | 17.81 ± 0.46 | 17.84 ± 0.55 | 0.2419 ± 0.0178 |
| 9 | 17.47 ± 0.38 | 22.17 ± 0.22 | 21.97 ± 0.64 | 0.2734 ± 0.0196 |
| 10 | 25.96 ± 0.31 | 34.94 ± 0.31 | 35.43 ± 0.90 | 0.2051 ± 0.0120 |
| 11 | 34.33 ± 0.51 | 47.21 ± 0.47 | 47.81 ± 0.85 | 0.1994 ± 0.0082 |

TABLE 4-continued

| Powder Formulation Number | Cumulative % Insulin Released at 6 hr | Cumulative % Insulin Released at 24 hr | Maximum‡ Release at 24 hr (Cumulative %) | First Order‡ Release Constants ($hr^{-1}$) |
|---|---|---|---|---|
| 12 | 61.78 ± 0.33 | 68.56 ± 0.23 | 65.20 ± 3.34 | 0.5759 ± 0.0988 |
| 13 | 78.47 ± 0.40 | 85.75 ± 0.63 | 84.9 ± 3.81 | 0.5232 ± 0.0861 |

‡$Release_{(t)} = Release_{(inf)} * (1 - e^{-k*t})$
†Used as a control formulation.

The data presented in Table 4 show that for insulin containing powder formulations employing the positively charged lipid DPePC (Formulations 4 and 6–11) and DSePC (Formulations 2 and 3), first order release constants similar to that observed with the slow release injectable insulin formulation, Humulin L, can be achieved. Further, the first order release constants of these same formulations is significantly lower than that observed with the fast release injectable insulin formulation, Humulin R. As such, sustained release dry powder insulin formulations having varying compositions of positively charged lipid can be formulated.

Preparation of Estrone Sulfate—Containing Powder Formulations

The estrone sulfate powder formulations listed in Table were prepared as follows. Pre-spray drying solutions were prepared by dissolving the lipin in ethanol and estrone sulfate and leucine in water. The ethanol solution was then mixed with the water solution at a ration 70/30 ethanol/water. Final total solute concentration of the solution used for spray drying varied from 1 g/L to 3 g/L. As an example, the DPePC/leucine/estrone sulfate (76/20/4) spray drying solution was prepared by dissolving 760 mg of DPePC in 700 mL of ethanol, dissolving 200 mg of leucine and 40 mg of estrone sulfate in 300 mL of water and then mixing the two solutions to yield one liter of cosolvent with a total solute concentration of 1 g/L (w/v). Higher solute concentrations of, for example, 3 g/L (w/) were prepared by dissolving three times more of each solute in the same volumes of ethanol and water The mixture was spray dried following the procedure described above for the insulin containing powder formulation. During spray drying, the feed rate was about 50 mL/min, the inlet temperature ranged from about 110° C. to about 120° C., and the outlet temperature was about 52° C.

The physical characteristic of the estrone sulfate containing powders is set forth in Table 5. The MMAD and VMGD were determined as detailed above.

TABLE 5

| POWDER FORMULATION NUMBER | COMPOSITIONS (% WEIGHT BASIS) | MMAD (μm)§ | VMGD (μm)¶ | DENSITY (g/cc)‡ |
|---|---|---|---|---|
| 16 | DPePC (Avanti)/Leucine/ Estrone Sulfate (sodium salt) = 76/20/4 | 5.9 | 16.0 | 0.136 |
| 17 | DPPC/Leucine/ Estrone Sulfate (sodium salt) = 76/20/4 | 3.7 | 12.7# | 0.085 |

†Used as a control for comparison for in vivo studies
§Mass median aerodynamic diameter
¶Volumetric median geometric diameter at 2 bar pressure
#Measured using Coulter Multisizer
‡Determined using $d_{aer} = d_g \sqrt{\rho}$ The data presented in Table 5 showing the physical characteristics of the formulations comprising estrone sulfate are predictive of the respirability of the formulations. That is, as discussed above the large geometric diameters, small aerodynamic diameters and low densities possessed by the powder prepared as described herein render the particles respirable.

In Vivo Experiments—Estrone Sulfate Containing Powders

The following experiment was performed to determine the rate and extent of estrone sulfate absorption into the blood stream of rats following pulmonary administration of dry powder formulations comprising estrone sulfate.

The nominal estrone-sulfate dose administered was 40 μg per rat, in 1 mg of powder. Male Sprague-Dawley rats were obtained from Taconic Farms (Germantown, N.Y.). At the time of use, the animals weighed an average of 415 g (±10 g S.E.M.). The animals were allowed free access to food and water.

The powders were delivered to the lungs using an insufflator device for rats (PennCentury, Philadelphia, Pa.). The powder amount was transferred into the insufflator sample chamber. The delivery tube of the insufflator was then inserted through the mouth into the trachea and advanced until the tip of the tube was about a centimeter from the carina (first bifurcation). The volume of air used to deliver the powder from the insufflator sample chamber was 3 mL, delivered from a 10 mL syringe. In order to maximize powder delivery to the rat, the syringe was recharged and discharged two more times for a total of three air discharges per powder dose.

Catheters were placed into the jugular veins of the rats the day prior to dosing. At sampling times, blood samples were drawn from the jugular vein catheters and immediately transferred to EDTA coated tubes. Sampling times were 0, 0.25, 0.5, 1, 2, 4, and 6 hours after powder administration. After centrifugation, plasma was collected from the blood samples. Plasma samples were stored at 4° C. if analysis was performed within 24 hours or at −75° C. if analysis would occur later than 24 hours after collection.

Table 6 contains the estrone sulfate plasma levels quantified using the assay described above.

TABLE 6

| | PLASMA ESTRONE-SULFATE CONCENTRATION (ng/mL) ± S.E.M. | |
|---|---|---|
| TIME (HRS) | FORMULATION 16 | FORMULATION 17 |
| 0 | 0.07 ± 0.02 | 0.08 ± 0.05 |
| 0.25 | 12.07 ± 1.96 | 22.26 ± 8.96 |
| 0.5 | 18.88 ± 2.21 | 23.39 ± 12.72 |
| 1 | 12.20 ± 3.31 | 10.59 ± 0.61 |

TABLE 6-continued

| TIME (HRS) | PLASMA ESTRONE-SULFATE CONCENTRATION (ng/mL) ± S.E.M. FORMULATION 16 | FORMULATION 17 |
|---|---|---|
| 2 | 4.65 ± 0.77 | 3.45 ± 0.63 |
| 4 | 4.02 ± 1.42 | 0.86 ± 0.10 |
| 6 | 1.49 ± 0.48 | 0.33 ± 0.12 |
| n | 4 | 3 |

Figure 3:
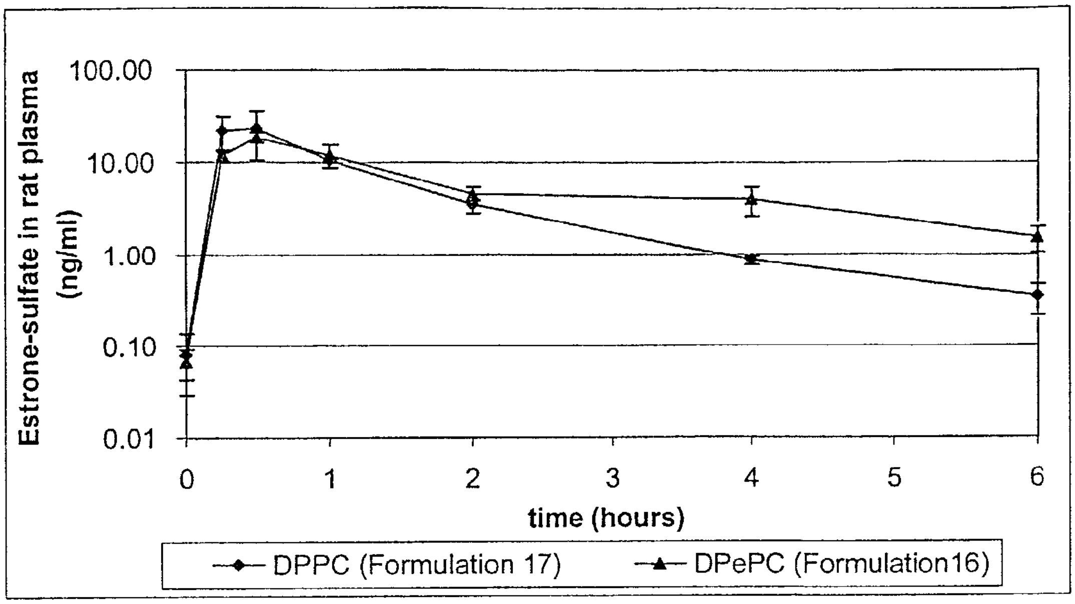
FIG. 3 is a graph showing the in vivo release profile of dry powder formulation comprising estrone sulfate (−) and either a lipid with no overall net charge (DPPC) or a lipid having an overall charge opposite (DPePC, +) to that of the estrone sulfate.

The results presented in Table 6 and depicted graphically in FIG. 3, show that the formulation comprising DPePC (overall positive charge) and estrone sulfate (negative charge) exhibited sustained release of estrone sulfate when compared to the formulation employing the lipid DPPC (no overall net charge) and estrone sulfate. Specifically, at six hours post administration, the plasma level of estrone sulfate for the DPePC containing formulation was 1.49±0.48 ng/mL as compared to 0.33±0.12 ng/mL for the DPPC containing formulation.

Preparation of Albuterol—Containing Powder Formulations

The albuterol sulfate powder formulations listed in Table 7, were prepared as follows. Pre-spray drying solutions were prepared by dissolving the lipid in ethanol and albuterol sulfate and leucine in water. The ethanol solution was then mixed with the water solution at a ratio of 70/30 ethanol/water. Final total solute concentration of the solution used for spray drying varied from 1 g/L to 3 g/L. As an example, the DPPC/leucine/albuterol sulfate (76/16/8) spray drying solution was prepared by dissolving 760 mg of DPPC in 700 mL of ethanol, dissolving 160 mg leucine and 870 mg of albuterol sulfate in 300 mL water and then mixing the two solutions to yield one liter of cosolvent with a total solute concentration of 1 g/L (w/v). Higher solute concentrations of 3 g/L (w/v) were prepared by dissolving three times more of each solute in the same volumes of ethnaol and water. The solution was spray-dried as described above for the insulin containing formulation. Specifically, the inlet temperature was from about 110° C. to about 140° C., and the outlet temperature ranged from about 45–57° C.

The physical characteristics of the albuterol sulfate containing powders is set forth in Table 7. The MMAD and VMGD were determined as detailed above.

TABLE 7

| POWDER FORMULATION NUMBER | COMPOSITIONS (% WEIGHT BASIS) | MMAD (μm)§ | VMGD (μm)¶ | DENSITY (g/cc)‡ |
|---|---|---|---|---|
| 18 | DSPC/Leucine/ Albuterol Sulfate= 76/16/8 | 3.3 | 6.1 | 0.293 |
| 19 | DSPG/Leucine/ Albuterol Sulfate = 76/16/8 | 4.1 | 6.4 | 0.410 |
| 20 | DPPC/Leucine/ Albuterol Sulfate = 76/23/1 | 2.8 | 12.0 | 0.054 |
| 21 | DPPG/Leucine/ Albuterol Sulfate = 76/16/8 | 3.3 | 7.1 | 0.216 |

†Used as a control for comparison in either in vitro or in vivo studies
§Mass median aerodynamic diameter
¶Volumetric median geometric diameter at 2 bar pressure
‡Determined using $d_{aer} = d_g \sqrt{\rho}$ The data presented in Table 7 showing the physical characteristics of the formulations comprising albuterol sulfate are predictive of the respirability of the formulations. That is, as discussed above the large geometric diameters, small aerodynamic diameters and low densities possessed by the formulations prepared as described herein render the formulations respirable.

In Vivo Testing of Albuterol Sulfate Formulations

A whole-body plethysmography method for evaluating pulmonary function in guinea pigs was used to assess the sustained effects of the albuterol sulfate formulations listed in Table 7.

The system used was the BUXCO whole-body unrestrained plethysmograph system with BUXCO XA pulmonary function software (BUXCO Electronics, Inc., Sharon, Conn.). The method was conducted as described by Silbaugh S. A. and Mauderly, J. L., in American Physiological Society, Vol. 84:1666–1669 (1984) and Chang, B. T., et al in Journal of Pharmacological and Toxicological Methods, Vol. 39(3):163–168 (1998). This method allows individual animals to be challenged repeatedly over time with methacholine given by nebulization. A calculated measurement of airway resistance based on flow parameters, the enhanced pause PenH was used as a marker for protection from methacholine-induced bronchoconstriction. Baseline pulmonary function (airway hyperresponsiveness) values were measured prior to any experimental treatment. Airway hyperresponsiveness was then assessed in response to saline and methacholine at various timepoints (2–3, 16 and 24 hours) following administration of albuterol-sulfate formulations. Average PenH is calculated from data collected between 4 and 9 minutes following challenge with saline or methacholine. The percent of baseline PenH at each timepoint is calculated for each experimental animal. Values from animals that received the same albuterol sulfate formulation were subsequently averaged to determine the mean group response (±standard error) at each timepoint.

The nominal dose of albuterol-sulfate administered was 50 μg for the DPPG-based formulation (#21) and 25 μg for the DPPC-based formulation (#20). To achieve those nominal doses, the total weights of powder administered were 0.625 mg and 2.5 mg, respectively.

Male Hartley guinea pigs were obtained from Elm Hill Breeding Labs (Chelmsford, Mass.). At the time of use, the animals weighed an average of 363 g (±5 g S.E.M.). The animals were allowed free access to food and water. The powder amount was transferred into the insufflator sample chamber (insufflation device for guinea pigs, Penn Century, Philadelphia, Pa.). The delivery tube of the insufflator was inserted through the mouth into the trachea and advanced until the tip of the tube was about a centimeter from the carina (first bifurcation). The volume of the air used to deliver the powder from the insufflator sample chamber was 3 mL, delivered from a 10 mL syringe. In order to maximize powder delivery to the guinea pig, the syringe was recharged and discharged two more times for a total of three air discharges per powder dose. Methacholine challenges were performed at time points 2–3, 16 and 24 hours after administration.

Figure 4:
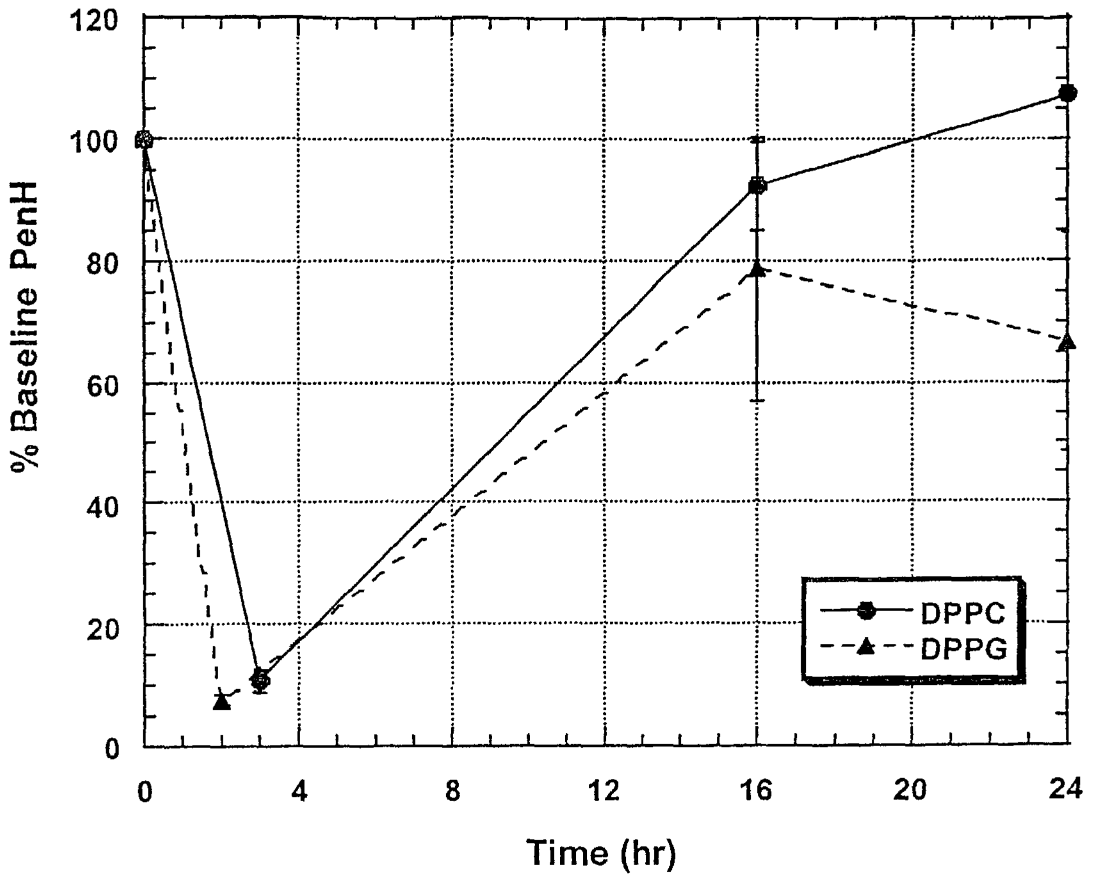
FIG. 4 is a graph of percent of PenH above baseline versus time following administration of dry powder formulations of albuterol sulfate and lipid in animals which have been challenged repeatedly over time with methacholine given by nebulization.

FIG. 4 shows that the formulation comprising DPPG (overal negative charge) and albuterol sulfate (overall positive charge) provided sustained protection against methacholine-induced bronchoconstriction when compared to the formulation comprising DPPC (no overall net charge) and albuterol sulfate for at least 24 hours following administration.

In another experiment, as much as 200 μg of albuterol sulfate in a DPPC-based formulation did not provide prolonged protection against induced bronchoconstriction.

In Vitro Release Studies—Albuterol Sulfate

Controlled Release Studies of Albuterol Sulfate were conducted using the COSTAR™ Brand Transwell Inserts, With Plates, Sterile. The plates were equipped with 6 wells having an area of 4.7 $cm^2$. The insert size was 24 mm, the pore size was 3.0 μm. A predetermined amount of the powder to be tested (approximately 10–15 mg) was placed into a HPMC Size #2 capsule. The capsule was then placed inside an inhaler and the powder was sprayed on the Transwell insert using an in-house vacuum system. Formulations were run in triplicate.

After spraying, the insert was placed inside the Transwell plate containing a volume of 1.8 mL of Phosphate Buffered Saline (pH=7.4) which had previously been equilibrated at 37° C. for 30 minutes. The Transwell plate was hermetically sealed in order to prevent evaporation of the buffer during the experiment.

The Transwell Experiment was carried out in an incubator at 37° C. on an orbital shaker at a speed of 100 $min^{-1}$. At specified time-points throughout the experiment, 1.8 mL of phosphate buffered saline was removed from the Transwell plate. The inserts were then placed into a new Transwell plate containing 1.8 mL of fresh phosphate buffered saline. Typical Transwell experiments are conducted for 4 hours. Samples are withdrawn after 5 min., 15, min., 30, min., 1 h, 1.5 h, 2 h, 3 h, and 4 h.

The amount of albuterol sulfate in the PBS buffer sampled at predetermined in vitro release time points was quantitated using a RP-HPLC method with Phenomenex Luna 5 μ, C8(2), 250×4.6 mm column (Torrance, Calif.) and UV detection at 275 nm.

Table 8 summarizes the in vitro release data and first order release constants for the powder formulations of Table 7 comprising albuterol sulfate. The first order release constants for the powder formulation comprising DSPG (negatively charged) and albuterol sulfate is about 4 time slower compared to the powder formulation comprising DSPC (no net overall charge) and albuterol sulfate (positive).

TABLE 8

| Powder Formulation Number | Compositions (% weight basis) | Cumulative % Insulin Released at 4 hr | Maximum Release at 4 hr (Cumulative %)‡ | First Order Release Constants ($hr^{-1}$)‡ |
|---|---|---|---|---|
| 18 | DSPC/Leucine/Albuterol Sulfate (sodium salt) = 76/16/8 | 106.21 ± 1.73 | 105.64 ± 0.20 | 29.7360 ± 0.7504 |
| 19 | DSPG/Leucine/Albuterol Sulfate (sodium salt) = 76/16/8 | 97.44 ± 0.68 | 95.13 ± 1.39 | 7.9334 ± 0.6877 |

‡$Release_{(t)} = Release_{(mf)} * (1 - e^{-k*t})$
†Used as a control formulation.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for delivery via the pulmonary system comprising:

administering to the respiratory tract of a patient in need of treatment, prophylaxis or diagnosis an effective amount of particles comprising:

a bioactive agent in association with a charged lipid wherein the charged lipid has an overall net positive charge, the agent has an overall net negative charge upon association, the agent is not a nucleic acid and wherein release of the agent is sustained.

2. The method of claim 1, wherein association of the agent and charged lipid comprises an ionic complexation.

3. The method of claim 2, wherein association of the lipid and agent further comprises hydrogen bonding.

4. The method of claim 1, wherein the charge ratio of lipid to bioactive agent is from about 0.25:1 to about 1:0.25.

5. The method of claim 4, wherein the charge ratio of lipid to bioactive agent is from about 0.5:1 to about 1:0.5.

6. The method of claim 5, wherein the charge ratio of lipid to bioactive agent is about 1:1.

7. The method of claim 1, wherein the bioactive agent is a protein.

8. The method of claim 7, wherein the protein is insulin.

9. The method of claim 8, wherein the sustained release is at least about 6 hours post administration.

10. The method of claim 1, wherein the lipid is a 1,2-diacyl-sn-glycero-3-alkylphosphocholine or a 1,2-diacyl-sn-glycero-3-alkylphosphoalkanolamine.

11. The method of claim 10 wherein the 1,2-diacyl-sn-glycero-3-alkylphosphocholine lipid is represented by Formula III:

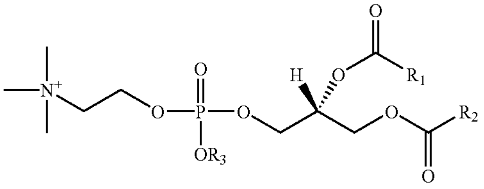

wherein, $R_1$ and $R_2$ are independently an aliphatic group having from about 3 to about 24 carbons; and $R_3$ is an aliphatic group having from about 1 to about 24 carbons.

12. The method of claim 10, wherein the 1,2-diacyl-sn-glycero-3-alkylphosphocholine is 1,2-dipalmitoyl-sn-glycero-3-ethylphosphocholine (DPePC), 1,2-dimyristoyl-sn-glycero-3-ethylphosphocholine(DMePC), 1,2-distearoyl-sn-glycero-3-ethylphosphocholine(DSePC), 1,2-dilauroyl-sn-glycero-3-ethyiphosphocholine (DLePC), 1,2-dioleoyl-sn-glycero-3-ethylphosphocholine(DOePC) or any combination thereof.

13. The method of claim 10, wherein the 1,2-diacyl-sn-glycero-3-alkylphosphoalkanolamine is represented by Formula IV:

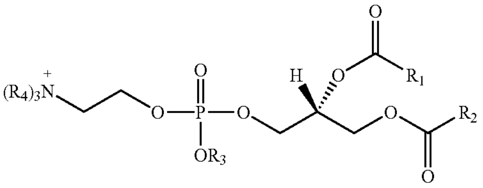

wherein, $R_1$ and $R_2$ are independently an aliphatic group having from about 3 to about 24 carbons;

$R_3$ is an aliphatic group having from about 1 to about 24 carbons; and $R_4$ is independently hydrogen or an aliphatic group having from about 1 to about 6 carbons.

14. The method of claim 10, wherein the 1,2-diacyl-sn-glycero-3-alkylphosphoalkanolamine is 1,2-dipalmitoyl-sn-glycero-3-ethylethanolamine(DPePE), 1,2-dimyristoyl-sn-glycero-3-ethylphosphoethanolamine(DMePE), 1,2-distearoyl-sn-glycero-3-ethylphosphoethanolamine (DSePE), 1,2-dilauroyl-sn-glycero-3-ethylphosphoethanolamine (DLePE), 1,2-dioleoyl-sn-glycero-3-ethylphosphoethanolamine(DOePE) or any combination thereof.

15. The method of claim 1 wherein the particles have a tap density less than about 0.4 $g/cm^3$.

16. The method of claim 15, wherein the particles have a tap density less than about 0.1 $g/cm^3$.

17. The method of claim 1, wherein the particles have a median geometric diameter of from about 5 micrometers and about 30 micrometers.

18. The method of claim 1, wherein the particles have an aerodynamic diameter of from about 1 to about 5 microns.

19. The method of claim 18, wherein the particles have an aerodynamic diameter of from about 1 to about 3 microns.

20. The method of claim 18, wherein the particles have an aerodynamic diameter of from about 3 to about 5 microns.

21. The method of claim 1, wherein delivery to the pulmonary system includes delivery to the deep lung.

22. The method of claim 1, wherein delivery to the pulmonary system includes delivery to the central airways.

23. The method of claim 1, wherein delivery to the pulmonary system includes delivery to the upper airways.

24. The method of claim 1, wherein the particles further comprise a lipid having no overall net charge.

25. The method of claim 1 wherein the particles further comprise a carboxylic acid or salt thereof.

26. The method of claim 25, wherein the carboxylic acid includes at least two carboxyl groups.

27. The method of claim 1, wherein the particles further comprise a multivalent metal salt or ionic components thereof.

28. The method of claim 27, wherein the multivalent salt is a salt of an alkaline earth metal.

29. The method of claim 1, wherein the particles further comprise an amino acid.

30. The method of claim 29, wherein the amino acid is hydrophobic.

31. The method of claim 30, wherein the hydrophobic amino acid is leucine, isoleucine, alanine, valine, phenylalanine or any combination thereof.

32. A method for delivery via the pulmonary system comprising:

administering to the respiratory tract of a patient in need of treatment an effective amount of particles comprising:

insulin in association with a charged lipid wherein the charged lipid has an overall net positive charge which is opposite to the overall net negative charge of the insulin upon association and wherein release of the insulin is sustained.

33. The method of claim 32, wherein the lipid is a 1,2-diacyl-sn-glycero-3-alkylphosphocholine or a 1,2-diacyl-sn-glycero-3-alkylphosphoalkanolamine.

34. The method of claim 33, wherein the 1,2-diacyl-sn-glycero-3-alkylphosphocholine is 1,2-dipalmitoyl-sn-glycero-3-ethylphosphocholine(DPePC), 1,2-dimyristoyl-sn-glycero-3-ethylphosphocholine(DMePC), 1,2-distearoyl-sn-glycero-3-ethylphosphocholine(DSePC), 1,2-dilauroyl-sn-glycero-3-ethylphosphocholine (DLePC), 1,2-dioleoyl-sn-glycero-3-ethylphosphocholine(DOePC) or any combination thereof.

35. The method of claim 33, wherein the 1,2-diacyl-sn-glycero-3-alkylphosphoalkanolamine is 1,2-dipalmitoyl-sn-glycero-3-ethylethanolamine(DPePE), 1,2-dimyristoyl-sn-glycero-3-ethylphosphoethanolamine(DMePE), 1,2-distearoyl-sn-glycero-3-ethylphosphoethanolamine (DSePE), 1,2-dilauroyl-sn-glycero-3-ethylphosphoethanolamine (DLePE), 1,2-dioleoyl-sn-glycero-3-ethylphosphoethanolamine(DOePE) or any combination thereof.

36. The method of claim 32, wherein association of the agent and charged lipid comprises an ionic complexation.

37. The method of claim 36, wherein association of the lipid and agent further comprises hydrogen bonding.

38. The method of claim 32, wherein the charge ratio of lipid to bioactive agent is from about 0.25:1 to about 1:0.25.

39. The method of claim 38, wherein the charge ratio of lipid to bioactive agent is from about 0.5:1 to about 1:0.5.

40. The method of claim 39, wherein the charge ratio of lipid to bioactive agent is about 1:1.

41. The method of claim 32, wherein the particles further comprise a carboxylic acid.

42. The method of claim 32, wherein the particles further comprise an amino acid.

43. The method of claim 32, wherein the particles further comprise a lipid with no overall net charge.

44. The method of claim 32, wherein the particles further comprise a multivalent metal salt or ionic components thereof.

45. The method of claim 32, wherein delivery to the pulmonary system includes delivery to the deep lung.

46. The method of claim 32, wherein delivery to the pulmonary system includes delivery to the central airways.

47. The method of claim 32, wherein delivery to the pulmonary system includes delivery to the upper airways.

* * * * *